United States Patent
Ema et al.

(10) Patent No.: US 9,211,534 B2
(45) Date of Patent: Dec. 15, 2015

(54) METALLOPORPHYRIN COMPLEX, MANUFACTURING PROCESS THEREFOR AND CARBON DIOXIDE FIXATION CATALYST THEREFROM, AS WELL AS PROCESS FOR MANUFACTURING CYCLIC CARBONATE

(71) Applicant: National University Corporation Okayama University, Okayama-shi (JP)

(72) Inventors: Tadashi Ema, Okayama (JP); Takashi Sakai, Okayama (JP); Yuki Miyazaki, Okayama (JP)

(73) Assignee: NATIONAL UNIVERSITY CORPORATION OKAYAMA UNIVERSITY, Okayama (JP)

( * ) Notice: Subject to any disclaimer, the term of this patent is extended or adjusted under 35 U.S.C. 154(b) by 0 days.

(21) Appl. No.: 14/345,657

(22) PCT Filed: Sep. 19, 2012

(86) PCT No.: PCT/JP2012/073957
§ 371 (c)(1),
(2) Date: Mar. 19, 2014

(87) PCT Pub. No.: WO2013/042695
PCT Pub. Date: Mar. 28, 2013

(65) Prior Publication Data
US 2014/0228561 A1    Aug. 14, 2014

(30) Foreign Application Priority Data

Sep. 21, 2011 (JP) .................................. 2011-206623

(51) Int. Cl.
*C07D 487/22* (2006.01)
*B01J 31/22* (2006.01)
*C07D 317/36* (2006.01)
(Continued)

(52) U.S. Cl.
CPC .......... *B01J 31/2295* (2013.01); *B01J 31/0239* (2013.01); *B01J 31/0244* (2013.01); *B01J 31/0268* (2013.01); *B01J 31/183* (2013.01); *C07D 317/36* (2013.01); *C07D 487/22* (2013.01); *C07F 9/5442* (2013.01); *C07F 9/5449* (2013.01); *C07F 9/6561* (2013.01); *B01J 2231/341* (2013.01); *B01J 2531/025* (2013.01); *B01J 2531/16* (2013.01); *B01J 2531/22* (2013.01); *B01J 2531/26* (2013.01); *B01J 2531/42* (2013.01); *B01J 2531/845* (2013.01); *B01J 2531/847* (2013.01); *B01J 2531/98* (2013.01); *B01J 2540/42* (2013.01); *B01J 2540/54* (2013.01)

(58) Field of Classification Search
CPC .................................................. C07D 487/22
See application file for complete search history.

(56) References Cited

U.S. PATENT DOCUMENTS

| 4,663,467 | A | 5/1987 | Kruper, Jr. et al. |
| 5,283,356 | A | 2/1994 | Marquis et al. |

(Continued)

FOREIGN PATENT DOCUMENTS

| CN | 101514195 | A | 8/2009 |
| CN | 102164987 | A | 8/2011 |

(Continued)

OTHER PUBLICATIONS

Ishikawa et al.Zinc(II)-5,10,15,20-tetrakis($\alpha$-pyridino-m-tolyl)porphyrin Tetrabromide, Molbank, 2009, 4, M637.*

(Continued)

*Primary Examiner* — Brian McDowell
(74) *Attorney, Agent, or Firm* — Buchanan, Ingersoll & Rooney PC

(57) ABSTRACT

There is provided a metalloporphyrin complex represented by general formula (1):

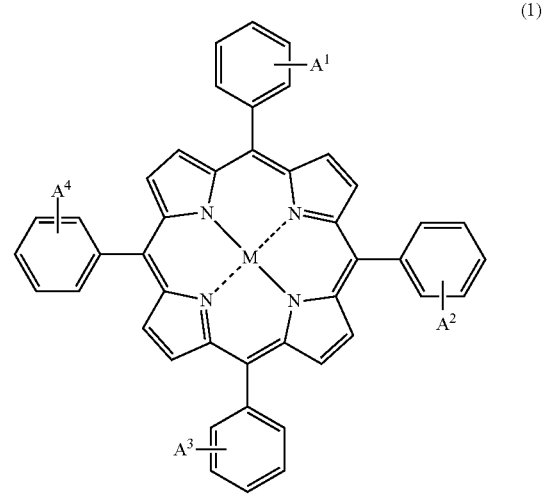

wherein M is a metal; $A^1$ to $A^4$ are independently of each other a substituent represented by general formula (2):

$$-D-E^+X^- \qquad (2)$$

wherein D is a divalent organic group having 1 to 20 carbon atoms; $E^+$ is a quaternary ammonium group or quaternary phosphonium group having 3 to 60 carbon atoms; and X is a halogen atom. There is thus provided a metalloporphyrin complex which, when used as a carbon dioxide fixation catalyst, exhibits high catalytic activity, has a small environmental burden and can be easily synthesized.

5 Claims, 1 Drawing Sheet

(51) Int. Cl.
| | |
|---|---|
| C07F 9/54 | (2006.01) |
| C07F 9/6561 | (2006.01) |
| B01J 31/02 | (2006.01) |
| B01J 31/18 | (2006.01) |

(56) References Cited

U.S. PATENT DOCUMENTS

| | | |
|---|---|---|
| 5,994,339 A | 11/1999 | Crapo et al. |
| 2006/0040914 A1 | 2/2006 | Roncucci et al. |
| 2011/0152497 A1 | 6/2011 | Allen et al. |

FOREIGN PATENT DOCUMENTS

| | | |
|---|---|---|
| GB | 2352449 B | 6/2003 |
| JP | 56-127384 A | 10/1981 |
| JP | 59-101488 A | 6/1984 |
| JP | 11-509180 A | 8/1999 |
| JP | 2006-512301 A | 4/2006 |

OTHER PUBLICATIONS

International Search Report (PCT/ISA/210) mailed on Dec. 11, 2012, by the Japanese Patent Office as the International Searching Authority for International Application No. PCT/JP2012/073957.
W.J. Kruper et al., Catalytic Formation of Cyclic Carbonates from Epoxides and $CO_2$ with Chromium Metalloporphyrinates, J. Org. Chem, 1995, 60, pp. 725-727.
Robert L. Paddock et al., Co(III) porphyrin/DMAP: an efficient catalyst system for the synthesis of cyclic carbonates from $CO_2$ and epoxides, Tetrahedron Letters 45, 2004, pp. 2023-2026.
R. Srivastava, et al., Factors affecting activation and utilization of carbon dioxide in cyclic carbonates synthesis over Cu and Mn peraza macrocyclic complexes, Journal of Molecular Catalysis A: Chemical 226, 2005, pp. 199-205.
Lili Jin et al., Metal porphyrin/phenyltrimethylammonium tribromide: High efficient catalysts for coupling reaction of $CO_2$ and epoxides, Journal of Molecular Catalysis A: Chemical 261, 2007, pp. 262-266.
Mei Wang et al., Efficient Solvent-free Synthesis of Chloropropene Carbonate from the Coupling Reacting of $CO_2$ and Epichlorohydrin Catalyzed by Magnesium Porphyrins as Chlorophyll-like Catalysts, Chinese Journal of Chemical Engineering, 19(3), 2011, pp. 446-451.
Ying Liu et al., Functional multiwalled carbon nanotube nanocomposite with iron picket-fence porphyrin and its electrocatalytic behavior, Electrochemistry Communications 9, 2007, pp. 2564-2570.
N. Robic et al., Synthesis and Preliminary DNA-Interaction Studies of a New Cationic Porphyrin, Tetrahedron Letters, vol. 31, No. 33, 1990, pp. 4739-4742.
Takeshi Yamashita et al., Stabilization of guanine quadruplex DNA by the binding of porphyrins with cationic side arms, Bioorganic & Medicinal Chemistry 13, 2005, pp. 2423-2430.
Fatemeh Ahmadi et al., Electron-deficient tin(IV)tetraphenylporphyrin perchlorate: A highly efficient catalyst for chemical fixation of carbon dioxide, Polyhedron 32, 2012, pp. 68-72.
Fatemeh Ahmadi et al., Highly efficient chemical fixation of carbon dioxide catalyzed by high-valent tetraphenylporphyrinatotin(IV) triflate, Inorganic Chemistry Communications 14, 2011, pp. 1489-1493.
Tadashi Ema et al., A bifunctional catalyst for carbon dioxide fixation: cooperative double activation of epoxides for the synthesis of cyclic carbonates, Chemical Communication, vol. 48, No. 37, Dec. 11, 2012, pp. 4489-4491.
Schneider et al.: "DNA Interactions with Porphyrins Bearing Ammonium Side Chains," The Journal of Organic Chemistry, vol. 59, Issue 24, pp. 7473-7478, 1994.
Jin: "Study on the Synthesis of Metalloporphyrin and Multi-chiral Schiff-base Cobalt complexes and their Catalytic Properties in the Coupling Reaction of Carbon dioxide with Epoxides," CDFD, Engineering Science, vol. 1, Issue 12, pp. 40-48, 2009.
Zhang et al.: "Activation of Carbon Dioxide and Synthesis of Propylene Carbonate," Chinese Chemical Letters, vol. 13, Issue 11, pp. 1047-1050, 2002.
Bai et al.: "Bifunctional Metalloporphyrins-Catalyzed Coupling Reaction of Epoxides and $CO_2$ to Cyclic Carbonates," Chinese Journal of Catalysis, vol. 31, Issue 2, pp. 176-180, 2010.
Search Report issued in corresponding Chinese Patent Application No. 201280057181.0 on Feb. 27, 2015, with verified English Translation.

* cited by examiner

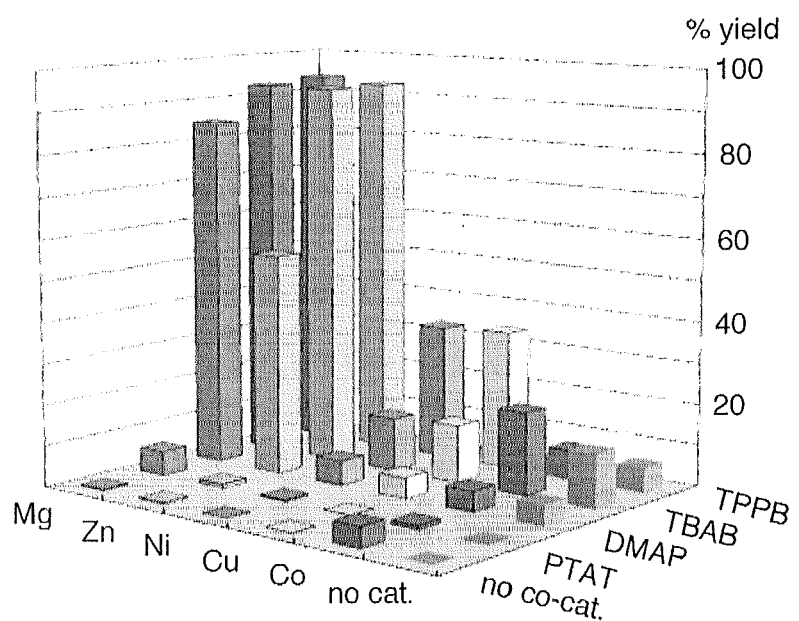

METALLOPORPHYRIN COMPLEX, MANUFACTURING PROCESS THEREFOR AND CARBON DIOXIDE FIXATION CATALYST THEREFROM, AS WELL AS PROCESS FOR MANUFACTURING CYCLIC CARBONATE

TECHNICAL FIELD

The present invention relates to a novel metalloporphyrin complex, a manufacturing process therefor and a carbon dioxide fixation catalyst therefrom. The carbon dioxide fixation catalyst can be suitably used for manufacturing a cyclic carbonate. The present invention also relates to a process for manufacturing a cyclic carbonate using a catalyst made of a metalloporphyrin complex or a metal phthalocyanine complex and a particular co-catalyst.

BACKGROUND ART

Hitherto, C1 carbon sources have been cyanide ions (or hydrocyanic acid), carbon monoxide, phosgene and so forth. These materials are, however, highly toxic. Therefore, an alternative chemical material has been desired. Carbon dioxide is a renewable C1 carbon source. However, carbon dioxide is low-reactive and thus, its applications have been limited.

Cyclic carbonates have been extensively used as an electrolyte for a lithium-ion secondary battery, a raw material for polycarbonates, a polar aprotic solvent or the like. Cyclic carbonates have been typically produced by a method using a 1,2-diol and phosgene as starting materials. Such a method has had the problems of the use of highly toxic phosgene and byproduction of corrosive hydrogen chloride gas over the years. In contrast, a synthetic process for producing a cyclic carbonate by coupling carbon dioxide with an epoxide is a very clean process associated with no byproducts. There have been described some catalysts which promote the reaction.

Non-patent Reference 1 has described a process for manufacturing a cyclic carbonate using a porphyrin complex with Cr as a central metal as a catalyst and N,N-dimethyl-4-aminopyridine (hereinafter, sometimes abbreviated as"DMAP") or N-methylimidazole as a co-catalyst. However, in this process, a reaction must be conducted under a high pressure of 5 MPa or more, resulting in difficulty in practical use.

Non-patent Reference 2 has described a process for manufacturing a cyclic carbonate using a porphyrin complex with Co as a central metal as a catalyst and DMAP, pyridine, N-methylimidazole, tricyclohexylphosphine oxide or triphenylphosphine as a co-catalyst. However, a reaction yield is sometimes low in the process. Using dichloromethane as a solvent, the process is environmentally unsound.

Non-patent Reference 3 has described a process for manufacturing a cyclic carbonate using a porphyrin complex or phthalocyanine complex with Cu as a central metal as a catalyst and DMAP as a co-catalyst. However, a reaction yield is sometimes low in the process. Using dichloromethane as a solvent, the process is environmentally unsound.

Non-patent Reference 4 has described a process for manufacturing a porphyrin complex with Co, Fe, Ru or Mn as a central metal and phenyltrimethylammonium tribromide (hereinafter, sometimes abbreviated as "PTAT"), tetrabutylammonium bromide or DMAP as a co-catalyst. However, a reaction yield is sometimes low in the process.

Non-patent Reference 5 has described a process for manufacturing a cyclic carbonate using a porphyrin complex with Mg as a central metal as a catalyst and triethylamine as a co-catalyst. However, a reaction yield is sometimes low in the process.

PRIOR ART REFERENCES

Non-Patent References

Non-patent Reference 1: W. J. Kruper et al., J. Org. Chem., 60, 725-727 (1995).
Non-patent Reference 2: R. L. Paddock et al., Tetrahedron Lett., 45, 2023-2026 (2004).
Non-patent Reference 3: R. Srivastava et al., J. Mol. Catal. A: Chem., 226, 199-205 (2005).
Non-patent Reference 4: L. Jin et al., J. Mol. Catal. A: Chem., 261, 262-266 (2007).
Non-patent Reference 5: W. Mei et al., Chinese Journal of Chemical Engineering, 19(3), 446-451(2011).

Problem to be Solved by the Invention

To solve the above problems, an objective of the present invention is to provide a novel metalloporphyrin complex which exhibits higher catalyst activity when being used as a carbon dioxide fixation catalyst, has a small environmental burden and can be easily synthesized. Another objective is to provide a process for manufacturing such a metalloporphyrin complex and a carbon dioxide fixation catalyst made of the complex. A further objective is to provide a process for manufacturing a cyclic carbonate with a high yield and a smaller environmental burden.

Means for Solving Problem

The above problems can be solved by providing a metalloporphyrin complex represented by general formula (1).

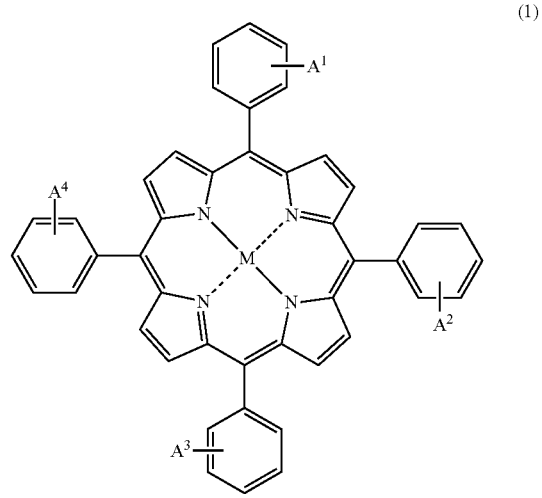

(1)

wherein M is metal; $A^1$ to $A^4$ are independently of each other a substituent represented by general formula (2):

$$-D-E^+X^- \quad (2)$$

wherein D is a divalent organic group having 1 to 20 carbon atoms; $E^+$ is a quaternary ammonium group or quaternary phosphonium group having 3 to 60 carbon atoms; and X is a halogen atom.

It is preferable that in general formula (2), E⁺ represents general formula (3)

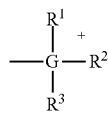
(3)

wherein G is a nitrogen atom or phosphorus atom; and $R^1$ to $R^3$ are independently of each other a monovalent organic group having 1 to 20 carbon atoms; or $R^1$ to $R^3$ may be linked together to form a ring.

It is also preferable that in general formula (2), D is an organic group represented by general formula (4):

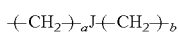
(4)

wherein J is an oxygen atom, —CO—O—, —O—CO—, a sulfur atom, —O—CO—NH—, —NH—CO—O—, —CO—NH—, —NH—CO— or a single bond; "a" is an integer of 0 or more; and "b" is an integer of 1 or more.

It is also preferable that the metalloporphyrin complex is represented by general formula (5):

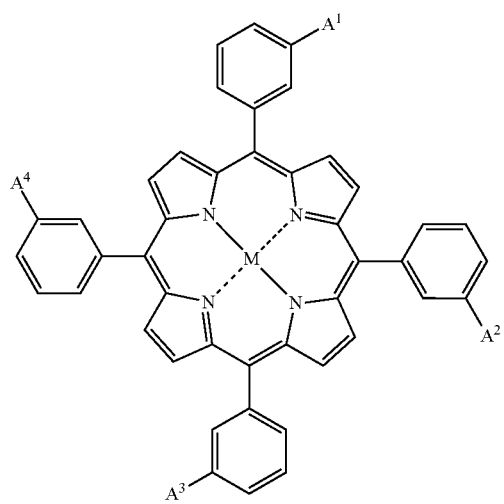
(5)

wherein M and $A^1$ to $A^4$ are as defined in general formula (1).

The above problems can be solved by a process for manufacturing the metalloporphyrin complex, comprising reacting a porphyrin represented by general formula (6):

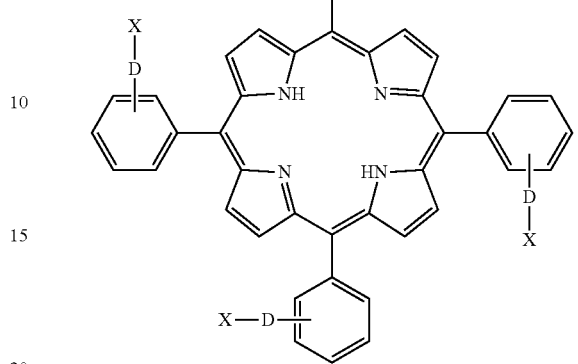
(6)

wherein D and X are as defined for general formula (2), with a salt of metal M, to form a metal complex represented by general formula (7):

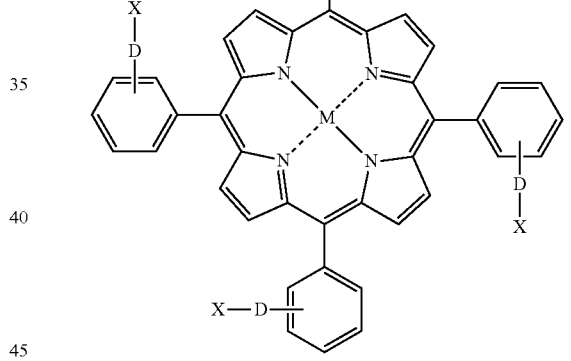
(7)

wherein M is as defined in general formula (1); and D and X are as defined in general formula (2); and then reacting the metal complex with a tertiary amine or tertiary phosphine to provide the metalloporphyrin complex represented by general formula (1).

A carbon dioxide fixation catalyst made of the metalloporphyrin complex is a suitable embodiment of the present invention. A more preferable embodiment is a process for manufacturing a cyclic carbonate, comprising reacting carbon dioxide with an epoxide represented by general formula (8):

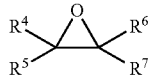
(8)

wherein $R^4$ to $R^7$ are independently of each other a hydrogen atom or a monovalent organic group having 1 to 20 carbon atoms; or $R^4$ to $R^7$ may be linked together to form a ring in the presence of the carbon dioxide fixation catalyst, to form a cyclic carbonate represented by general formula (9):

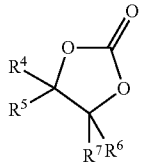

(9)

wherein $R^4$ to $R^7$ are as defined for general formula (8).

The above problems can be solved by providing a process for manufacturing a cyclic carbonate, comprising, in the presence of a catalyst made of the metalloporphyrin complex represented by general formula (10)

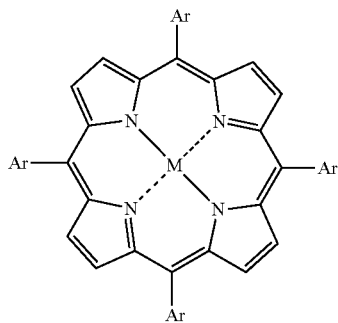

(10)

wherein M represents magnesium or zinc; and Ar represents an aromatic ring optionally having a substituent, and in the presence of a co-catalyst which is at least one selected from a quaternary ammonium monohalide, a quaternary phosphonium monohalide and a compound represented by general formula (11):

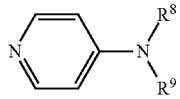

(11)

wherein $R^8$ and $R^9$ are independently of each other a monovalent organic group having 1 to 20 carbon atoms; or $R^8$ and $R^9$ may be linked together to form a ring, reacting carbon dioxide with an epoxide represented by general formula (8):

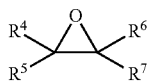

(8)

wherein $R^4$ to $R^7$ are independently of each other a hydrogen atom or a monovalent organic group having 1 to 20 carbon atoms; or $R^4$ to $R^7$ may be linked together to form a ring, to provide a cyclic carbonate represented by general formula (9):

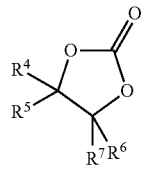

(9)

wherein $R^4$ to $R^7$ are as defined for general formula (8).

Herein, it is preferable that the quaternary ammonium monohalide and the quaternary phosphonium monohalide are represented by general formula (13):

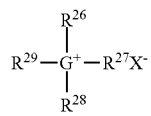

(13)

wherein X is a halogen atom; G is a nitrogen atom or a phosphorus atom; and $R^{26}$ to $R^{29}$ are independently of each other a monovalent organic group having 1 to 20 carbon atoms; or $R^{26}$ to $R^{29}$ may be linked together to form a ring.

The above problems can be also solved by providing a process for manufacturing a cyclic carbonate, comprising, in the presence of a complex which is a metal phthalocyanine complex represented by general formula (12):

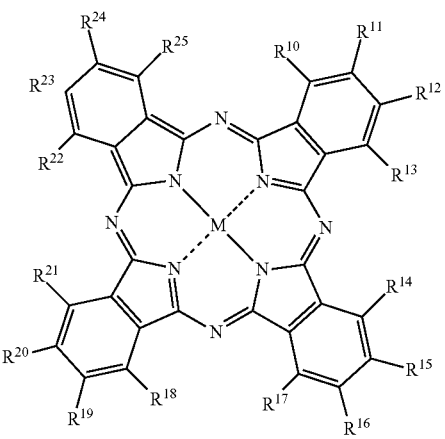

(12)

wherein M is magnesium or zinc; $R^{10}$ to $R^{25}$ are independently of each other a hydrogen atom, a monovalent hydrocarbon group having 1 to 20 carbon atoms or a halogen atom, and in the presence of a co-catalyst which is at least one selected from a quaternary ammonium monohalide, a quaternary phosphonium monohalide and a compound represented by general formula (11):

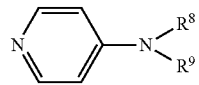

(11)

wherein $R^8$ and $R^9$ are independently of each other a monovalent organic group having 1 to 20 carbon atoms; or $R^8$ and $R^9$ may be linked together to form a ring, reacting carbon dioxide with an epoxide represented by general formula (8):

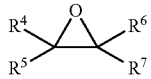

(8)

wherein $R^4$ to $R^7$ are independently of each other a hydrogen atom or a monovalent organic group having 1 to 20 carbon atoms; or $R^4$ to $R^7$ may be linked together to form a ring, to provide a cyclic carbonate represented by general formula (9):

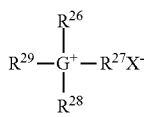

(9)

wherein $R^4$ to are as defined for general formula (8).

Herein, it is preferable that the quaternary ammonium monohalide and the quaternary phosphonium monohalide are represented by general formula (13):

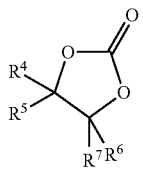

(13)

wherein X is a halogen atom; G is a nitrogen atom or a phosphorus atom; and $R^{26}$ to $R^{29}$ are independently of each other a monovalent organic group having 1 to 20 carbon atoms; or $R^{26}$ to $R^{29}$ may be linked together to form a ring.

Advantage of the Invention

A metalloporphyrin complex of the present invention exhibits higher catalyst activity when being used as a carbon dioxide fixation catalyst, has a small environmental burden and can be easily synthesized. It can be, therefore, suitably used for fixing carbon dioxide, particularly manufacturing a cyclic carbonate. A process for manufacturing a cyclic carbonate of the present invention is highly efficient and has a small environmental burden.

BRIEF DESCRIPTION OF THE DRAWINGS

FIG. 1 shows yields of cyclic carbonates.

BEST MODE FOR CARRYING OUT THE INVENTION

A metalloporphyrin complex of the present invention is represented by general formula (1). This compound is novel.

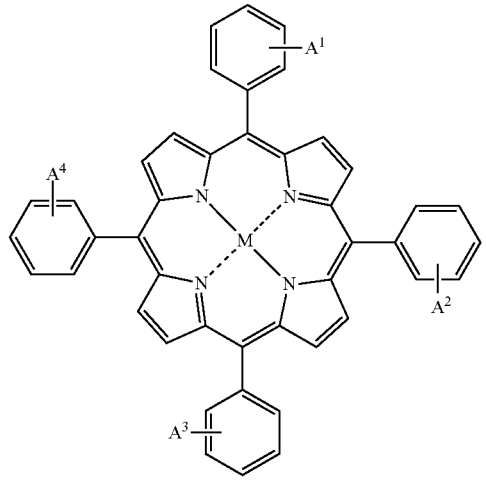

(1)

wherein M is metal; $A^1$ to $A^4$ are independently of each other a substituent represented by general formula (2):

-D-E$^+$X$^-$ (2)

wherein D is a divalent organic group having 1 to 20 carbon atoms; E$^+$ is a quaternary ammonium group or quaternary phosphonium group having 3 to 60 carbon atoms; and X is a halogen atom.

A metalloporphyrin complex of the present invention is characterized in that it has a quaternary ammonium group or quaternary phosphonium group represented by E$^+$. The substituent forms a quaternary ammonium salt or quaternary phosphonium salt with a halogen ion X$^-$. Such a salt is highly nucleophilic. When a metalloporphyrin complex of the present invention is used as a catalyst for synthesizing a cyclic carbonate, a central metal M in the complex acts as a Lewis acid and X$^-$ with E$^+$ as a counter ion acts as a nucleophile. Furthermore, since E$^+$ is bound to a porphyrin ring via a divalent organic group D, E$^+$ is moderately free and a distance between E$^+$ and the central metal M is proper. Thus, the metal M and X$^-$ with E$^+$ as a counter ion can simultaneously act on one molecule of a raw material. It significantly promotes the reaction.

In general formula (1), M is a metal. M has Lewis acidity. There are no particular restrictions to M as long as it is a metal, and it is suitably a divalent or trivalent metal exhibiting high catalyst activity when being used as a carbon dioxide fixation catalyst.

Examples of a divalent metal include magnesium, zinc, copper, nickel, cobalt and iron.

When it is a trivalent metal, M is a combination of a trivalent metal and a monovalent counter anion. Herein, examples of the trivalent metal include cobalt, iron, manganese, chromium and aluminum, and examples of the counter anion include halide anion and acetate anion.

M is more suitably a divalent metal. It is further suitably magnesium or zinc, particularly suitably magnesium.

In general formula (1), $A^1$ to $A^4$ are independently of each other a substituent represented by general formula (2).

In general formula (2), E$^+$ is a quaternary ammonium group or quaternary phosphonium group having 3 to 60 carbon atoms. The carbon number is suitably 3 to 30.

The quaternary ammonium group and quaternary phosphonium group are suitably represented by, but not limited to, general formula (3):

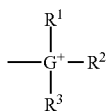
(3)

wherein G is a nitrogen atom or phosphorus atom; and $R^1$ to $R^3$ are independently of each other a monovalent organic group having 1 to 20 carbon atoms; or $R^1$ to $R^3$ may be linked together to form a ring, or, general formula (14):

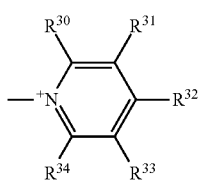
(14)

wherein $R^{30}$ to $R^{34}$ are independently of each other hydrogen atom or a monovalent hydrocarbon group having 1 to 20 carbon atoms; or $R^{30}$ to $R^{34}$ may be linked together to form a ring. Such a substituent is bulky. In synthesis of a cyclic carbonate using a metalloporphyrin complex of the present invention as a catalyst, bulkiness of the substituent $E^+$ allows $X^-$ with $E^+$ as a counter ion to further efficiently act, resulting in further improvement of catalyst activity.

In general formula (3), G is a nitrogen atom or phosphorus atom.

In general formula (3), $R^1$ to $R^3$ are independently of each other a monovalent organic group having 1 to 20 carbon atoms. The carbon number is suitably 2 or more. In the light of easy synthesis, the carbon number is suitably 10 or less.

Examples of the organic group include an optionally substituted alkyl group, an optionally substituted alkenyl group, an optionally substituted alkynyl group, an optionally substituted aryl group, an optionally substituted arylalkyl group, an optionally substituted arylalkenyl group, an optionally substituted arylalkynyl group, an optionally substituted cycloalkyl group and an optionally substituted heterocyclic group. Here, examples of a substituent include an alkyl group having 1 to 5 carbon atoms and a halogen atom. The organic group is suitably an optionally substituted alkyl group or an optionally substituted aryl group, more suitably an alkyl group or an aryl group.

Examples of an alkyl group include straight-chain alkyl groups such as a methyl group, an ethyl group, a n-propyl group, a n-butyl group and a n-pentyl group and branched alkyl groups such as an isopropyl group, an isobutyl group, a sec-butyl group, a tert-butyl group, an isopentyl group, a neo-pentyl group and a tert-pentyl group, particularly suitably a n-butyl group.

Examples of an aryl group include a phenyl group, a biphenyl group, a naphthyl group, an anthryl group or a phenanthryl group, particularly suitably a phenyl group.

$R^1$ to $R^3$ may be linked together to form a ring. The ring can be monocyclic or bicyclic. When it is monocyclic, the total number of carbons as ring members can be 2 to 40, suitably 3 to 20. When it is bicyclic, the total number of carbons as members of the bicyclic ring can be 3 to 60, suitably 5 to 30. Furthermore, some of the ring members can be heteroatoms such as a nitrogen atom and an oxygen atom.

In general formula (14), $R^{30}$ to $R^{34}$ are independently of each other a hydrogen atom or a monovalent hydrocarbon group having 1 to 20 carbon atoms. The hydrocarbon group suitably contains 2 or more carbon atoms. In the light of easiness in synthesis, the carbon number is suitably 10 or less.

Examples of a hydrocarbon group include an alkyl group, an alkenyl group, an alkynyl group, an aryl group, an arylalkyl group, an arylalkenyl group, an arylalkynyl group and a cycloalkyl group. In particular, an alkyl group is suitable.

$R^{30}$ to $R^{34}$ may be linked together to form a ring. The number of carbon atoms as ring members can be 2 to 40, suitably 3 to 20.

In the light of easy synthesis, $R^{30}$ to $R^{34}$ are suitably a hydrogen atom.

In general formula (2), D is a divalent organic group having 1 to 20 carbon atoms. D links a porphyrin ring to $E^+$ in general formula (2). $E^+$ is bound to a porphyrin ring via D, so that degree of freedom of $E^+$ is improved. Thus, it facilitates nucleophilic attack by $X^-$ with $E^+$ as a counter ion when a metalloporphyrin complex of the present invention is used as a catalyst for synthesis of a cyclic carbonate. It results in high catalyst activity.

In the light of degree of freedom of $E^+$, the carbon number of D is suitably 2 or more. If the carbon number of D is more than 20, it leads to a higher cost. The carbon number of D is suitably 15 or less.

In general formula (2), the organic group in D is suitably an organic group represented by general formula (4):

(4)

wherein J is an oxygen atom, —CO—O—, —O—CO—, a sulfur atom, —O—CO—NH—, —NH—CO—O—, —CO—NH—, —NH—CO— or a single bond; "a" is an integer of 0 or more; and "b" is an integer of 1 or more. Such an organic group is flexible, so that degree of freedom of $E^+$ is improved. Thus, it facilitates nucleophilic attack by $X^-$ with $E^+$ as a counter ion when a metalloporphyrin complex of the present invention is used as a catalyst for synthesis of a cyclic carbonate. It results in high catalyst activity. In general formula (4), J is an oxygen atom, —CO—O—, —O—CO—, a sulfur atom, —O—CO—NH—, —NH—CO—O—, —CO—NH—, —NH—CO— or a single bond. In the light of easy synthesis, J is suitably an oxygen atom, —CO—O— or —O—CO—, more suitably an oxygen atom. "a" is an integer of 0 or more, and "b" is an integer of 1 or more. In the light of easy synthesis, "a" is suitably 0. In other words, it is suitable that J is directly bound to a porphyrin ring.

In general formula (2), X is a halogen atom. X becomes an anion (that is, $X^-$), which forms a salt with $E^+$ in general formula (2). X is suitably, but not limited to, a bromine atom or an iodine atom, more suitably a bromine atom in the light of easy nucleophilic attack when a metalloporphyrin complex of the present invention is used as a catalyst for synthesis of a cyclic carbonate and so on.

In the light of easy synthesis, it is also suitable that in general formula (1), $A^1$ to $A^4$ are attached to a phenyl group at the same position. Furthermore, a binding position of $A^1$ to $A^4$ is meta or para of the phenyl group because no stereoisomers are formed during synthesis. Furthermore, for avoiding steric hindrance when a metalloporphyrin complex of the present invention is used as a catalyst for synthesis of a cyclic carbonate, a binding position of $A^1$ to $A^4$ is suitably meta or para of the phenyl group. More suitably, general formula (1) is represented by general formula (5):

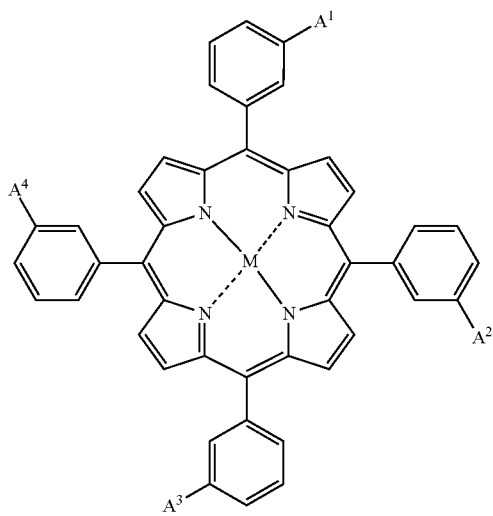

(5)

wherein M and A$^1$ to A$^4$ are as defined for general formula (1). It facilitates nucleophilic attack by X$^-$ with E$^+$ as a counter ion when a metalloporphyrin complex of the present invention is used as a catalyst for synthesis of a cyclic carbonate. It results in further higher catalyst activity.

In the light of easy synthesis, it is suitable that all of A$^1$ to A$^4$ are the same.

Although there are no particular restrictions to a process for manufacturing a metalloporphyrin complex of the present invention represented by general formula (1), a suitable synthesis process is a process comprising, reacting a salt of metal M with a porphyrin represented by general formula (6):

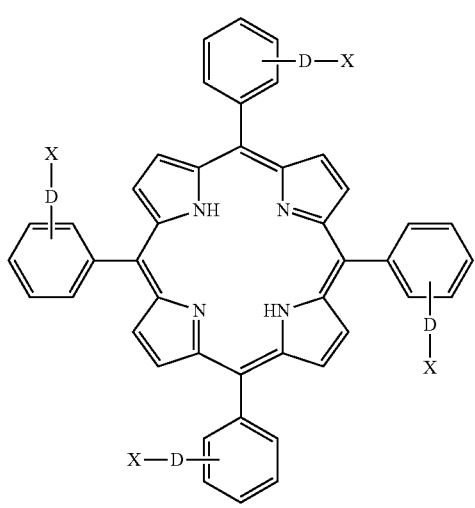

(6)

wherein D and X are as defined in general formula (2), to form a metal complex represented by general formula (7):

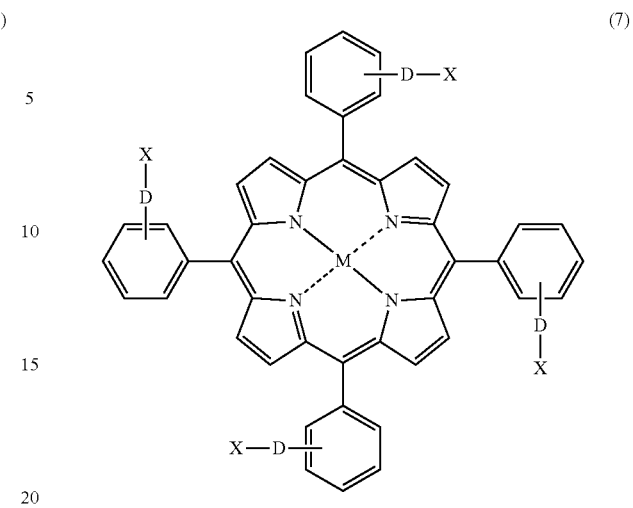

(7)

wherein M is as defined in general formula (1) and D and X are as defined in general formula (2), and then reacting the metal complex with a tertiary amine or tertiary phosphine to produce a metalloporphyrin complex represented by general formula (1). Here, metal M is as defined in general formula (1). A tertiary amine and a tertiary phosphine become an ammonium salt and a phosphonium salt, respectively, to form E$^+$ in general formula (2). In general, for forming a porphyrin complex, a porphyrin is reacted with a central metal in the final stage of a synthetic process. In contrast, a process of the present invention involves introducing metal M in a porphyrin represented by general formula (6) followed by reaction with a tertiary amine or tertiary phosphine, resulting in a higher yield of a metalloporphyrin complex. In this process, reaction steps are short and a reaction in each step is very common, so that a metalloporphyrin complex of the present invention can be easily produced. The process is, therefore, economically very advantageous.

A porphyrin represented by general formula (6) can be, for example, produced as described below. It is synthesized by reacting pyrrole with a benzaldehyde having a halogenated organic group using an acid catalyst such as trifluoroacetic acid and boron trifluoride diethyl ether complex (these can be used alone or in combination of two or more) for cyclization followed by oxidization using an oxidizing agent such as DDQ (2,3-dichloro-5,6-dicyano-p-benzoquinone). Here, a solvent can be dichloromethane. A reaction product can be purified by a common separation means such as column chromatography and recrystallization.

A method for introducing a central metal to a porphyrin represented by general formula (6) thus obtained can be appropriately selected, depending on the type of the central metal. For example, a porphyrin is mixed with a metal salt in a solvent to form a metal complex. And then, after adding water to wash out the metal salt, the complex can be obtained by purification by a common separation means such as column chromatography and recrystallization. It is suitable that in this reaction, 3 to 20 moles of the metal salt is mixed with one mole of the porphyrin. Examples of the solvent include chloroform, methanol and methylene chloride, which can be used alone or in combination of two or more. Generally, a reaction temperature can be appropriately selected within the range of 0 to 100° C.

A metalloporphyrin complex represented by general formula (1) can be formed by dissolving the metal complex represented by general formula (7) and a tertiary amine or tertiary phosphine in a solvent followed by stirring of the solvent. In this reaction, it is suitable that 4 to 30 moles of the tertiary amine or the tertiary phosphine is mixed with one mole of the metal complex. Examples of the solvent include chloroform and acetonitrile, which can be used alone or in combination of two or more. Generally, a reaction temperature can be appropriately selected within the range of 0 to 100° C. The reaction product can be purified by a common separation means such as column chromatography and recrystallization.

A carbon dioxide fixation catalyst made of a metalloporphyrin complex of the present invention thus obtained is a suitable embodiment. A metalloporphyrin complex of the present invention significantly promotes a synthetic reaction using carbon dioxide as a C1 carbon source. Carbon dioxide is renewable and safe C1 carbon source. Therefore, the use of carbon dioxide as a C1 carbon source is very advantageous, and is also preferable in the light of reduction in carbon dioxide emission. In particular, a metalloporphyrin complex of the present invention significantly promotes a reaction for synthesizing a cyclic carbonate from carbon dioxide and an epoxide.

A more suitable embodiment is a process for manufacturing a cyclic carbonate, comprising reacting carbon dioxide with an epoxide represented by general formula (8):

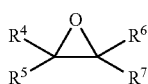

(8)

wherein $R^4$ to $R^7$ are independently of each other a hydrogen atom or a monovalent organic group having 1 to 20 carbon atoms; or $R^4$ to $R^7$ may be linked together to form a ring, in the presence of the carbon dioxide fixation catalyst, to provide a cyclic carbonate represented by general formula (9):

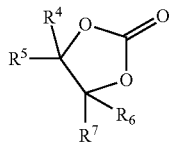

(9)

wherein $R^4$ to $R^7$ are as defined in general formula (8). Since this process proceeds in the absence of a solvent, a waste solvent is not generated and no byproducts are produced, so that an environmental burden is very small. Furthermore, a carbon dioxide fixation catalyst of the present invention has a very high catalyst activity in comparison with a conventional process using a porphyrin complex and a co-catalyst. An existing process using phosgene can be, therefore, replaced with the present process.

The above reaction can be conducted by placing an epoxide represented by general formula (8) and a metalloporphyrin complex represented by general formula (1) in an autoclave and then filling the vessel with carbon dioxide. The amount of the metalloporphyrin complex is suitably, but not limited to, 0.0001 to 0.1 mol % based on the epoxide (0.000001 to 0.001 mol of the metalloporphyrin complex based on 1 mol of the epoxide). An initial pressure in the vessel is suitably 0.1 to 5 MPa. A reaction temperature is suitably 10 to 200° C. According to the manufacturing process of the present invention, a cyclic carbonate can be efficiently produced under such mild conditions.

The following would be a mechanism of promoting a reaction of carbon dioxide with an epoxide by a metalloporphyrin complex of the present invention. The reaction mechanism will be described using the following chemical formula.

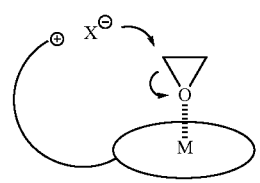

A central metal M in the metalloporphyrin complex acts as a Lewis acid, so that it is bound to oxygen in the starting epoxide and then $X^-$ with $E^+$ as a counter ion nucleophilically attacks a carbon in the epoxide, leading to ring opening of the epoxide. Here, it is assumed that the central metal M and $X^-$ with $E^+$ as a counter ion in one metalloporphyrin complex simultaneously act on the epoxide, to accelerate an ring-opening reaction of the epoxide as a rate-determining step in the reaction, resulting in significant acceleration of the reaction.

In general formula (8), $R^4$ to $R^7$ are independently of each other a hydrogen atom or a monovalent organic group having 1 to 20 carbon atoms. In the light of easy synthesis, the carbon number of the organic group is suitably 10 or less.

Examples of the organic group include an optionally substituted alkyl group, an optionally substituted alkenyl group, an optionally substituted alkynyl group, an optionally substituted aryl group, an optionally substituted arylalkyl group, an optionally substituted arylalkenyl group, an optionally substituted arylalkynyl group, an optionally substituted cycloalkyl group, an optionally substituted heterocyclic group, an alkoxy group, an aryloxy group, an aldehyde group, an optionally protected carboxyl group or its salt, an alkylcarbonyl group, an arylcarbonyl group, an alkyloxycarbonyl group, an aryloxycarbonyl group, an alkylcarbonyloxy group, an arylcarbonyloxy group, an alkylamino group, an arylamino group, an alkylammonium group, an aryl ammonium group, an alkylthio group, an arylthio group, an alkylsulfinyl group, an arylsulfinyl group, an alkylsulfonyl group, an arylsulfonyl group, an alkylazo group and an arylazo group. Here, a substituent can be, for example, an alkyl group having 1 to 5 carbon atoms or a halogen atom. The organic group is suitably an optionally substituted alkyl group.

$R^4$ to $R^7$ may be linked together to form a ring. The total carbon number as ring members can be 2 to 40, suitably 3 to 20. Furthermore, some of the ring members can be heteroatoms such as a nitrogen atom and an oxygen atom.

In the light of promotion of the reaction, it is suitable that any one of $R^4$ to $R^7$ is an organic group while the others are a hydrogen atom.

A cyclic carbonate represented by general formula (9) can be also very efficiently obtained by a manufacturing process, comprising, in the presence of a catalyst made of a metalloporphyrin complex represented by general formula (10):

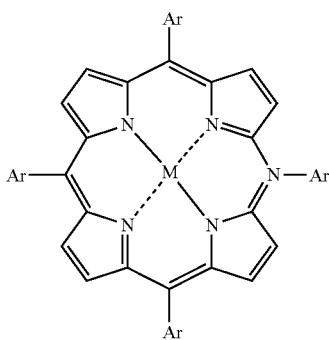

(10)

wherein M represents magnesium or zinc; and Ar represents an optionally substituted aromatic ring and a co-catalyst made of at least one selected from a quaternary ammonium monohalide, a quaternary phosphonium monohalide and a compound represented by general formula (11):

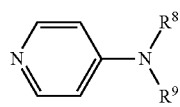

(11)

wherein $R^8$ and $R^9$ are independently of each other a monovalent organic group having 1 to 20 carbon atoms; or $R^8$ and $R^9$ may be linked together to form a ring, reacting carbon dioxide with an epoxide represented by general formula (8):

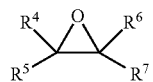

(8)

wherein $R^4$ to $R^7$ are as described above, to provide a cyclic carbonate represented by general formula (9):

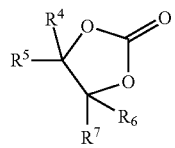

(9)

wherein $R^4$ to $R^7$ are as described above. Hereinafter, this process using a particular co-catalyst is sometimes referred to as "a two-component process using a metalloporphyrin complex". By using magnesium or zinc as a central metal in a porphyrin complex, catalyst activity can be significantly improved. The use of such a metal is an important feature of the two-component process. Since it has been believed that in general a magnesium or zinc complex is less active as a catalyst, it has not been used as a metal complex for a catalyst. It is, therefore, surprising that catalyst activity can be significantly improved by using an inexpensive common metal such as magnesium and zinc. Here, it is also important to use a co-catalyst made of at least one selected from a quaternary ammonium monohalide, a quaternary phosphonium monohalide and a compound represented by general formula (11).

In combination of the magnesium- or zinc-porphyrin complex described above with such a co-catalyst, catalyst activity is significantly improved.

The above reaction can be conducted by placing an epoxide represented by general formula (8), a metalloporphyrin complex represented by general formula (10) and a co-catalyst made of at least one selected from a quaternary ammonium monohalide, quaternary phosphonium monohalide and a compound represented by general formula (11) in an autoclave and then filling the vessel with carbon dioxide. The amount of the metalloporphyrin complex is suitably, but not limited to, 0.0001 to 1 mol % based on the epoxide (0.000001 to 0.01 mol of the metalloporphyrin complex to 1 mol of the epoxide). The amount of a co-catalyst is suitably, but not limited to, 0.0001 to 1 mol % based on an epoxide (0.000001 to 0.01 mol of the co-catalyst to 1 mol of the epoxide). The reaction conditions other than the amounts of the metalloporphyrin complex and the co-catalyst can be those for the process for manufacturing a cyclic carbonate using a carbon dioxide fixation catalyst made of a metalloporphyrin complex intramolecularly containing a quaternary ammonium group or quaternary phosphonium group represented by general formula (1) (hereinafter, sometimes referred to as a "bifunctional catalyst process").

In general formula (10), M is magnesium or zinc.

In general formula (10), Ar represents an optionally substituted aromatic ring. Examples of the aromatic ring include a phenyl group, a biphenyl group, a naphthyl group, an anthryl group and a phenanthryl group. In particular, a phenyl group is suitable. When the aromatic ring is substituted, examples of the substituent include an alkyl group having 1 to 5 carbon atoms and a halogen atom.

The quaternary ammonium monohalide and the quaternary phosphonium monohalide are suitably represented by general formula (13):

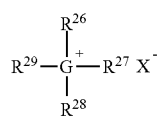

(13)

wherein G is as defined in general formula (3); $R^{26}$ to $R^{29}$ are independently of each other a monovalent organic group having 1 to 20 carbon atoms; or $R^{26}$ to $R^{29}$ may be linked together to form a ring; and X is as defined in general formula (2).

In general formula (13), $R^{26}$ to $R^{29}$ are independently of each other a monovalent organic group having 1 to 20 carbon atoms. $R^{26}$ to $R^{29}$ are as defined for $R^1$ to $R^3$ in general formula (3). $R^{26}$ to $R^{29}$ may be linked together to form a ring. The total number of carbon atoms as ring members can be 2 to 40, suitably 2 to 20. Some of the ring members can be heteroatoms such as a nitrogen atom and an oxygen atom.

In general formula (11), $R^8$ and $R^9$ are independently of each other a monovalent organic group having 1 to 20 carbon atoms. In the light of easy synthesis, the carbon number of $R^8$ and $R^9$ is suitably 10 or less. Examples of the organic group include an optionally substituted alkyl group, an optionally substituted alkenyl group, an optionally substituted alkynyl group, an optionally substituted aryl group, an optionally substituted arylalkyl group, an optionally substituted arylalkenyl group, an optionally substituted arylalkynyl group, an optionally substituted cycloalkyl group and an optionally substituted heterocyclic group. In particular, an alkyl group and an aryl group are more suitable.

Examples of the alkyl group include a methyl group, an ethyl group, a n-propyl group, a n-butyl group, a n-pentyl group, an isopropyl group, an isobutyl group, a sec-butyl group, a tert-butyl group, an isopentyl group, a neo-pentyl group and a tert-pentyl group. In particular, a methyl group which is inexpensive is suitable.

$R^8$ and $R^9$ may be linked together to form a ring. Here, the total carbon number of $R^8$ and $R^9$ can be 2 to 40, suitably 2 to 20. Furthermore, some of the ring members can be heteroatoms such as a nitrogen atom and an oxygen atom.

The epoxide represented by general formula (8) can be an epoxide used in a bifunctional catalyst process.

A metalloporphyrin complex represented by general formula (10) can be obtained by, but not limited to, a process comprising mixing a porphyrin and a metal salt in a solvent to form a metal complex followed by adding water for washing out the excessive metal salt. Suitably, the porphyrin can be commercially available. Thus, a cost can be further reduced. In a process for manufacturing a porphyrin represented by general formula (6) as a bifunctional catalyst process as described above, the complex can be obtained, substituting a proper aromatic aldehyde for a benzaldehyde having a halogenated organic group.

Furthermore, a cyclic carbonate represented by general formula (9) can be very efficiently obtained by a manufacturing process, comprising, in the presence of a complex made of a metal phthalocyanine complex represented by general formula (12)

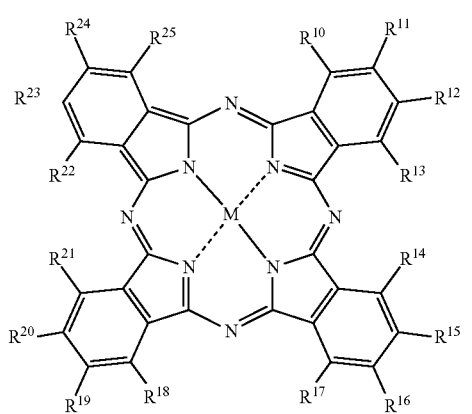

(12)

wherein M is magnesium or zinc; and $R^{10}$ to $R^{25}$ are independently of each other a hydrogen atom, a monovalent hydrocarbon group having 1 to 20 carbon atoms or a halogen atom, and a co-catalyst made of at least one selected from a quaternary ammonium monohalide, a quaternary phosphonium monohalide and a compound represented by general formula (11)

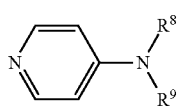

(11)

wherein $R^8$ and $R^9$ are as defined above, reacting carbon dioxide with an epoxide represented by general formula (8):

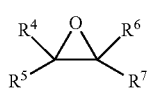

(8)

wherein $R^4$ to $R^7$ are as defined above, to obtain a cyclic carbonate represented by general formula (9):

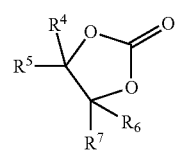

(9)

wherein $R^4$ to $R^7$ are as defined above. This process is the "two-component process using a metalloporphyrin complex" described above substituting a phthalocyanine for a porphyrin. Again, in this process, it seems to be important that a central metal M is magnesium or zinc and at least one selected from a quaternary ammonium monohalide, a quaternary phosphonium monohalide and a compound represented by general formula (11) is used as a co-catalyst.

The above reaction can be conducted by placing an epoxide represented by general formula (8), a complex made of metalloporphyrin complex represented by general formula (12) and a co-catalyst made of at least one selected from a quaternary ammonium monohalide, a quaternary phosphonium monohalide and a compound represented by general formula (1.1) in a pressure vessel such as an autoclave and then filling the vessel with carbon dioxide. The amount of the metal phthalocyanine complex is suitably, but not limited to, 0.0001 to 1 mol based on the epoxide (0.000001 to 0.01 mol of the metal phthalocyanine complex to 1 mol of the epoxide). The amount of the co-catalyst is suitably, but not limited to, 0.0001 to 1 mol % based on the epoxide (0.000001 to 0.01 mol of the co-catalyst to 1 mol of the epoxide). The reaction conditions other than the amounts of the metal phthalocyanine complex and the co-catalyst can be those for the bifunctional catalyst process described above.

In general formula (12), $R^{10}$ to $R^{25}$ are independently of each other a hydrogen atom, a monovalent hydrocarbon group having 1 to 20 carbon atoms or a halogen atom.

Examples of the hydrocarbon group include an alkyl group, an alkenyl group, an alkynyl group, an aryl group, an arylalkyl group, an arylalkenyl group, an arylalkynyl group and a cycloalkyl group. In particular, an alkyl group is suitable. In the light of easy synthesis, the carbon number of the hydrocarbon group is suitably 10 or less.

Suitably, $R^{10}$ to $R^{25}$ are a hydrogen atom or a halogen atom.

The co-catalyst and the starting epoxide are those used for the two-component process using the above metalloporphyrin complex.

There are no restrictions to a process for manufacturing a metal phthalocyanine complex represented by general formula (11). For example, it can be obtained by mixing a phthalocyanine with a metal salt in a solvent to form a metal complex and then adding water to wash out the excessive metal salt. Suitably, the phthalocyanine can be commercially available. Thus, a cost can be further reduced.

EXAMPLES

The present invention will be further detailed with reference to Examples.

The measuring apparatuses used for measurement are as follows.

Melting-point apparatus: Mettler Toledo, FP-62
IR spectrometer: Shimadzu, FTIR-8900
$^1$H NMR (600 MHz) spectrometer: Varian, Unity Inova AS600

$^{13}$C NMR (150 MHz) spectrometer: Varian, Unity Inova AS600

[1] Synthesis of a Bifunctional Catalyst 5,10,15,20-Tetrakis[3-(6-bromohexyloxy)phenyl]porphyrin (5a) was synthesized. The reaction formula is shown below.

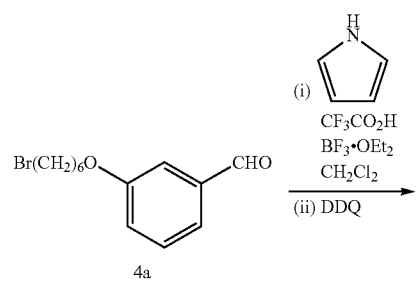

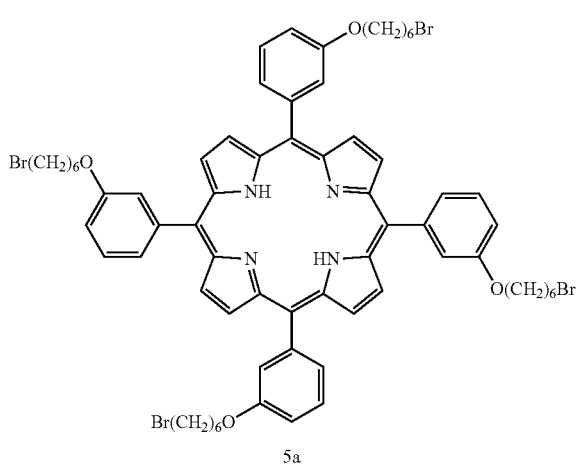

A solution of pyrrole (695 μL, 10.0 mmol) and 3-(6-bromohexyloxy)benzaldehyde (4a) (2.86 g, 10.0 mmol) dissolved in anhydrous methylene chloride (1.0 L) was bubbled with argon, and to the mixture were added boron trifluoride-diethyl etherate complex (12 μL, 0.097 mmol) and trifluoroaceLic acid (670 μL, 9.02 mmol). This mixed solution was stirred at room temperature for 4 hours under dark conditions. To the solution was added 2,3-dichloro-5,6-dicyano-1,4-benzoquinone (2.27 g, 10.0 mmol), and the mixture was stirred for additional 9 hours. To the reaction mixture was added triethylamine (1.0 mL, 7.2 mmol), and the mixture was concentrated. The residual material was purified by silica gel column chromatography [chloroform/hexane (2:1)] to give compound 5a (purple solid) (yield: 1.73 g, 52%).

$^1$H NMR (deuterochloroform, 600 MHz) −2.80 (s, 2H), 1.55 (br s, 16H), 1.89-1.92 (m, 16H), 3.41 (t, J=6.8 Hz, 8H), 4.15 (t, J=6.4 Hz, 8H), 7.32 (dd, J=2.3, 8.5 Hz, 4H), 7.63 (t, J=7.9 Hz, 4H), 7.77 (s, 4H), 7.81 (d, J=7.1 Hz, 4H), 8.90 (s, 811)

$^{13}$C NMR (deuterochloroform, 150 MHz, 50° C.) 25.4, 28.0, 29.2, 32.7, 33.5, 68.2, 114.3, 120.0, 121.4, 127.5, 127.6, 131.1, 143.6, 146.7, 157.6

IR (potassium bromide) 3317, 3063, 2932, 2862, 1589, 1466, 1435, 1342, 1281, 1173, 1042, 972, 926, 795, 733, 648 cm$^{-1}$ Anal. Calcd for $C_{68}H_{74}Br_4N_4O_4$: C, 61.36; H, 5.60; N, 4.21. Found: C, 60.99; H, 5.76; N, 4.11

MS (FAB) calcd for $C_{68}H_{75}{}^{79}Br_2{}^{81}Br_2N_4O_4$ 1331.2. Found 1331.3 (M+H)

5,10,15,20-Tetrakis[3-(6-bromohexyloxy)phenyl]porphyrin zinc(II) (6a) was synthesized. The reaction formula is shown below.

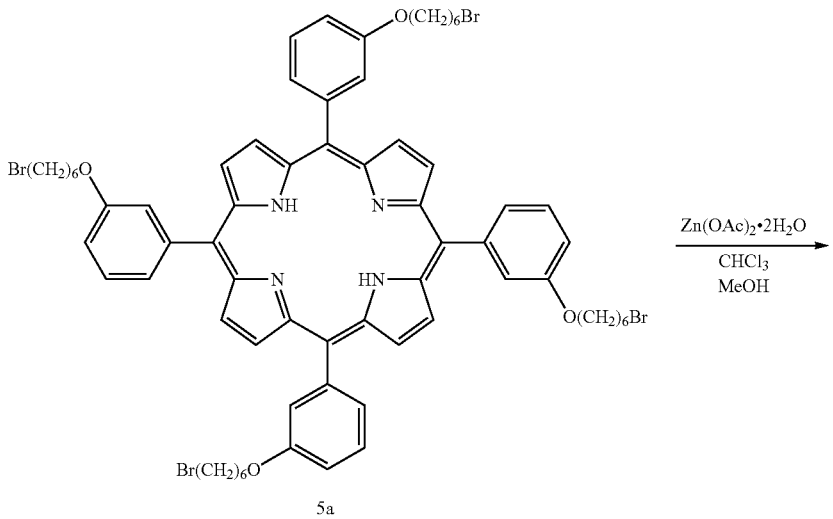

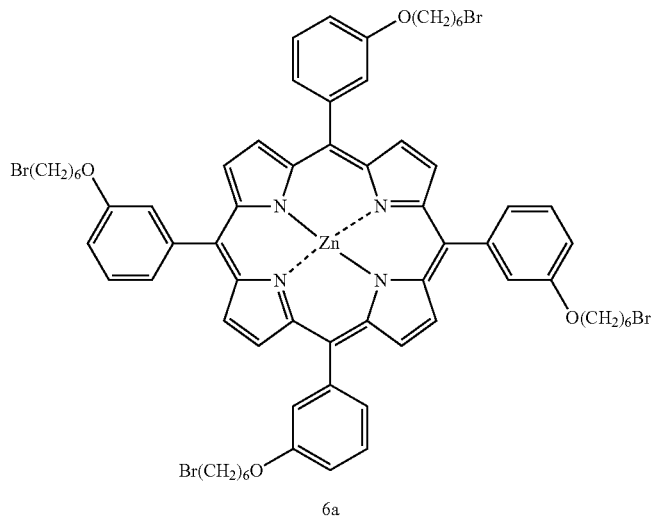

6a

A porphyrin 5a (266 mg, 0.200 mmol) was dissolved in anhydrous chloroform, and the mixture was stirred at 70° C. for 45 min under a nitrogen atmosphere. To the mixture was added zinc acetate dihydrate (439 mg, 2.00 mmol) dissolved in anhydrous methanol (4 mL), and the mixture was stirred at 70° C. for 4 hours. The mixture was cooled to room temperature, concentrated and then washed with water. The mixture was dried over sodium sulfate and concentrated. The residual material was purified by silica gel column chromatography [methylene chloride/hexane (2:1)], to give compound 6a (purple-red solid) (yield: 272 mg, 98%).

$^1$H NMR (deuterochloroform, 600 MHz) 1.53-1.55 (m, 16H), 1.88-1.90 (m, 16H), 3.40 (t, J=6.8 Hz, 8H), 4.11-4.15 (m, 8H), 7.30-7.32 (m, 4H), 7.63 (t, J=7.9 Hz, 4H), 7.76-7.77 (m, 4H), 7.81 (d, J=7.3 Hz, 4H), 9.00 (s, 8H)

$^{13}$C NMR (deuterochloroform, 150 MHz) 25.3, 27.9, 29.1, 32.6, 33.7, 67.9, 114.0, 120.9, 121.0, 127.3, 127.5, 132.0, 144.0, 150.1, 157.1

IR (potassium bromide) 3062, 2936, 2858, 1597, 1578, 1477, 1435, 1339, 1285, 1258, 1184, 1049, 999, 937, 799, 721, 702, 648 cm$^{-1}$ Anal. Calcd for $C_{68}H_{72}Br_4N_4O_4Zn$: C, 58.57; H, 5.20; N, 4.02. Found: C, 58.65; H, 5.25 N, 3.70

MS (FAB) calcd for $C_{68}H_{73}{}^{79}Br_2{}^{81}Br_2N_4O_4{}^{64}Zn$ 1393.2. Found 1393.2 (M+H)

5,10,15,20-Tetrakis[3-(6-triphenylphosphoniohexyloxy)phenyl]porphyrin zinc(II) tetrabromide (1a) was synthesized. The reaction formula is shown below.

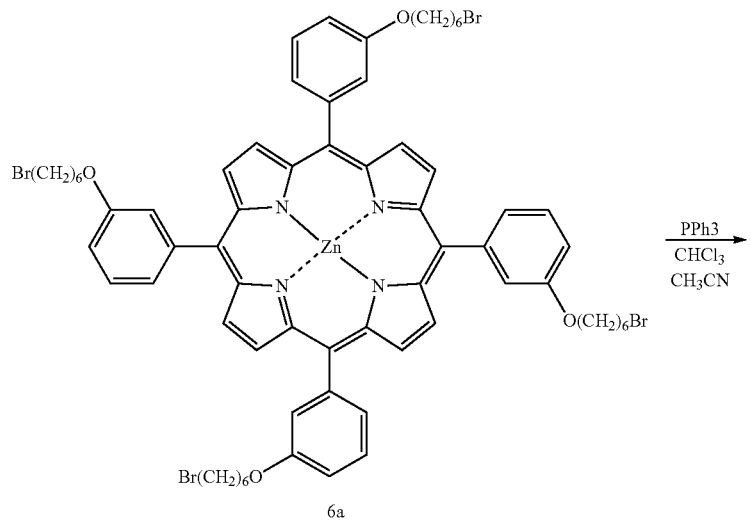

6a

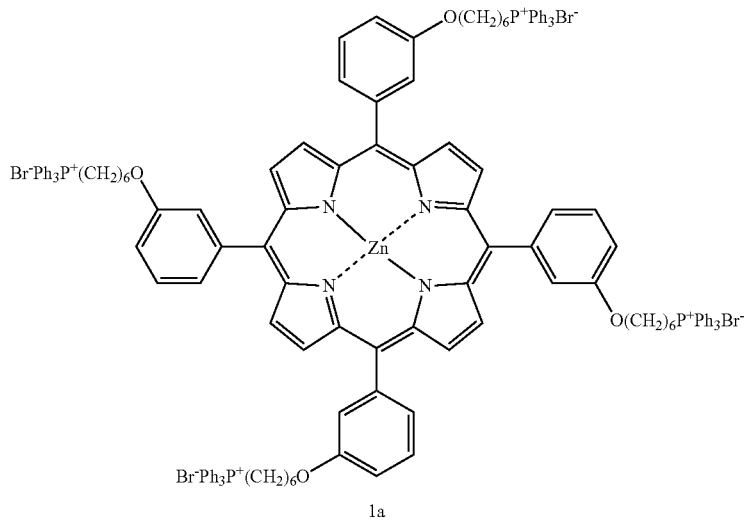

1a

Compound 6a (139 mg, 0.100 mmol) and triphenylphosphine (315 mg, 1.20 mmol) were dissolved in a mixed solvent of anhydrous chloroform (1 mL) and anhydrous acetonitrile (1 mL), and under dark conditions, the mixture was stirred at 70° C. for 48 hours under an argon atmosphere. The reaction solution was cooled to room temperature and concentrated. The crude product was washed with diethyl ether and filtrated. Recrystallization (methylene chloride/diethyl ether) gave zinc-porphyrin complex 1a (purple solid) (yield: 207 mg, 85%).

$^1$H NMR ($d_6$-dimethylsulfoxide, 600 MHz) 1.50-1.55 (m, 24H), 1.74-1.81 (m, 8H), 3.59 (br s, 8H), 4.13 (br s, 8H), 7.35-7.36 (m, 4H), 7.66-7.83 (m, 72H), 8.78 (s, 8H)

$^{13}$C NMR (deuterated methanol, 150 MHz) 22.4 (d, $J_{CP}$=51.6 Hz), 23.3, 26.3, 29.8, 30.9 (d, $J_{CP}$=15.6 Hz), 68.8, 114.2, 119.7 (d, $J_{CP}$=85.7 Hz), 121.6, 122.8, 120.4, 128.6, 131.4 (d, $J_{CP}$=12.6 Hz), 132.6, 134.6 (d, =9.7 Hz), 136.0, 145.8, 151.2, 158.5

$^{31}$P NMR (deuterated methanol, 243 MHz) 24.2

IR (potassium bromide) 3055, 2932, 2862, 1582, 1474, 1435, 1327, 1281, 1173, 1111, 1057, 995, 934, 787, 725, 687 cm$^{-1}$ HRMS (EST) calcd for $C_{140}H_{132}{}^{81}Br_3N_4O_4P_4{}^{64}Zn$ 2363.5979. Found 2363.5986 (M−Br)

5,10,15,20-Tetrakis[3-(6-tributylammoniohexyloxy)phenyl]porphyrin zinc(II) tetrabromide (1c) was synthesized. The reaction formula is shown below.

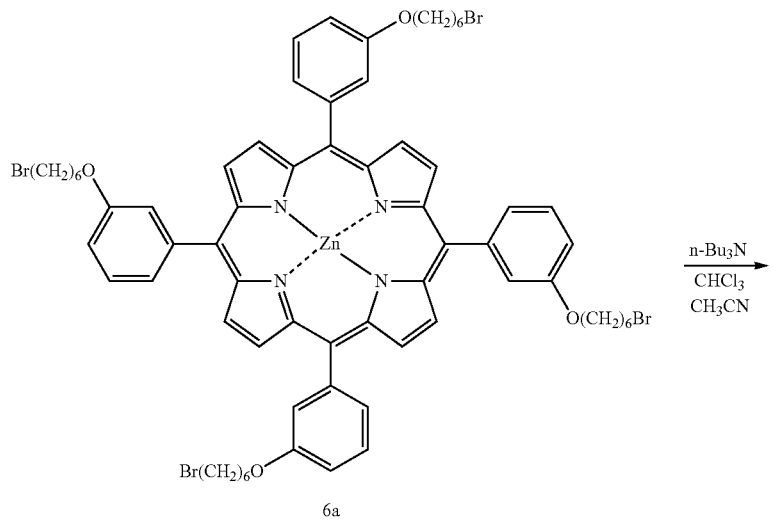

6a

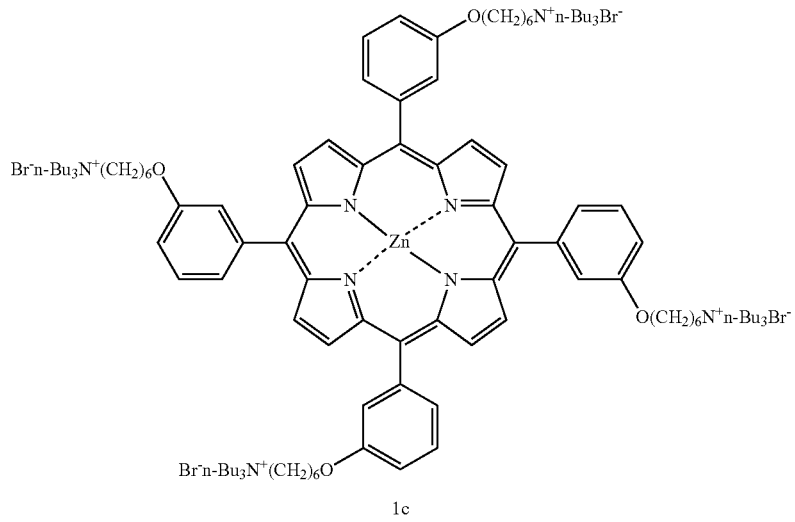

1c

Compound 6a (110 mg, 0.0788 mmol) and tributylamine (0.45 mL, 1.9 mmol) were dissolved in a mixed solvent of anhydrous chloroform (0.79 mL) and anhydrous acetonitrile (0.79 mL), and under dark conditions, the mixture was stirred at 70° C. for 90 hours under a nitrogen atmosphere. The reaction solution was cooled to room temperature and concentrated. The tributylamine layer was removed by a pipette. To the mixture was added methylene chloride and the mixture was washed with water containing 0.5% hydrobromic acid and sodium bromide. The mixture was dried over sodium sulfate and concentrated. Recrystallization (methylene chloride/diethyl ether) gave zinc-porphyrin complex 1c (purple solid) (yield: 123 mg, 73%).

$^1$H NMR (deuterated methanol, 600 MHz) 0.92-0.97 (m, 36H), 1.31-1.64 (m, 72H), 1.89 (br s, 8H), 3.11-3.20 (m, 32H), 4.19-4.20 (m, 8H), 7.34-7.35 (m, 4H), 7.62-7.65 (m, 4H), 7.73-7.77 (m, 8H), 8.85 (s, 8H)

$^{13}$C NMR (deuterated methanol, 150 MHz) 14.0, 20.5, 22.58, 22.62, 24.6, 26.6, 26.9, 30.1, 59.3, 68.9, 114.3, 121.6, 122.7, 128.4, 128.6, 132.7, 145.9, 151.3, 158.7

IR (potassium bromide) 3063, 2936, 2870, 1597, 1574, 1474, 1431, 1385, 1335, 1285, 1258, 1180, 1049, 995, 937, 880, 791, 718, 702 cm$^{-1}$ 5, 10, 15, 20-Tetrakis [3-(6-bromohexyloxy) phenyl]porphyrin magnesium (II) (6b) was synthesized. The reaction formula is shown below.

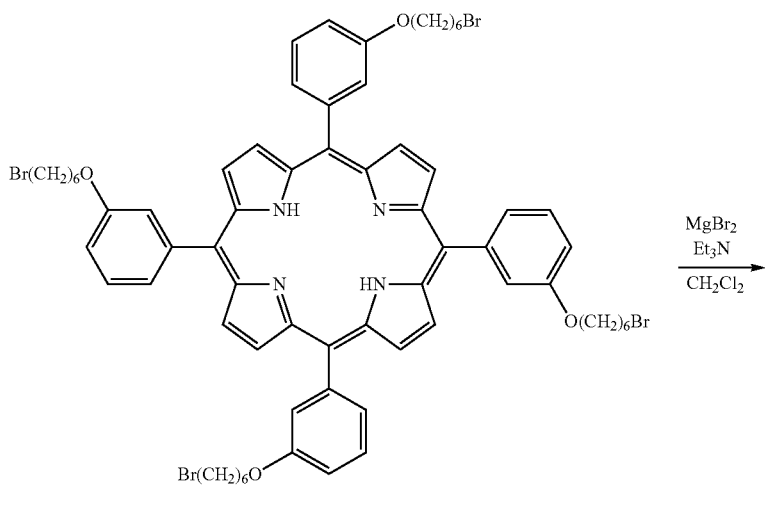

5a

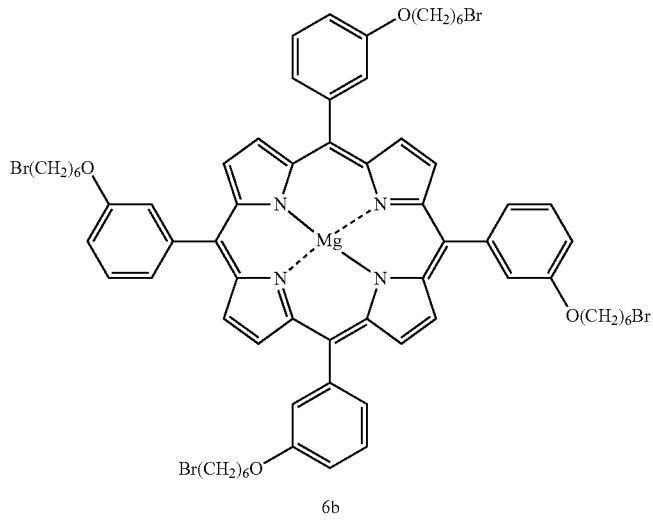

6b

Under a nitrogen atmosphere, a mixture of compound 5a (266 mg, 0.200 mmol) and magnesium bromide (368 mg, 2.00 mmol) in anhydrous methylene chloride (17 mL) were stirred at room temperature for 5 min. Triethylamine (1.7 mL, 12 mmol) was added and the mixture was stirred at room temperature for 30 min. The mixed solution was washed with 0.5% hydrochloric acid and water. The mixture was dried over sodium sulfate and concentrated. Recrystallization (methylene chloride/hexane) gave compound 6b (purple solid) (yield: 261 mg, 96%).

10H NMR (deuterochloroform, 600 MHz) 1.53-1.54 (m, 16H), 1.86-1.91 (m, 16ticles), 3.40 (t, J=6.8 Hz, 8H), 4.14 (t, J=6.4 Hz, 8H), 7.29 (dd, J=2.0, 8.4 Hz, 4H), 7.60 (t, J=7.9 Hz, 4H), 7.78 (br s, 4H), 7.81 (d, J=7.6 Hz, 4H), 8.91 (s, 8H)

$^{13}$C NMR (deuterochloroform, 150 MHz, 50° C.) 25.3, 27.9, 29.1, 32.7, 33.5, 68.3, 113.9, 121.3, 121.7, 126.9, 128.0, 131.8, 145.1, 149.9, 156.9

IR (potassium bromide) 3055, 2932, 2862, 1666, 1597, 1474, 1427, 1389, 1335, 1281, 1180, 1049, 995, 941, 880, 795, 725, 640 cm$^1$ Anal. Calcd for $C_{68}H_{72}Br_4MgN_4O_4$: C, 60.35; H, 5.36; N, 4.14. Found: C, 60.12; H, 5.48; N, 3.76

MS (FAB) calcd for $C_6H_{73}{}^{79}Br_2{}^{81}Br_2Mg_4O_4$ 1353.2. Found 1353.2 (M+H)

5,10,15,20-Tetrakis[3-(6-triphenylphosphoniohexyloxy)phenyl]porphyrin magnesium (II) tetrabromide (1b) was synthesized. The reaction formula is shown below.

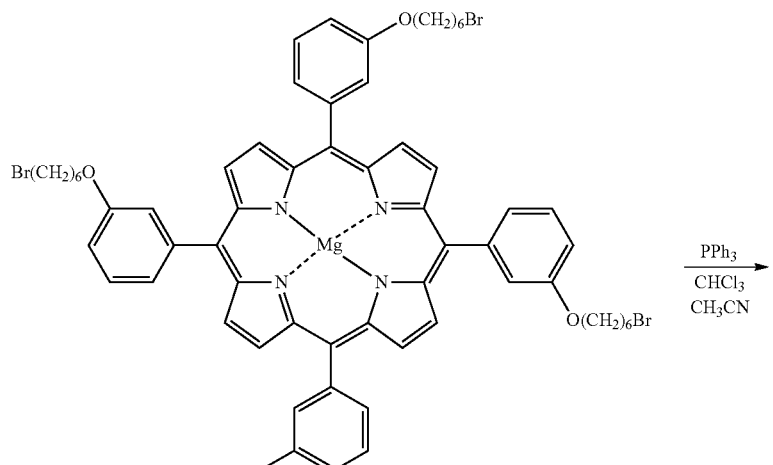

6b

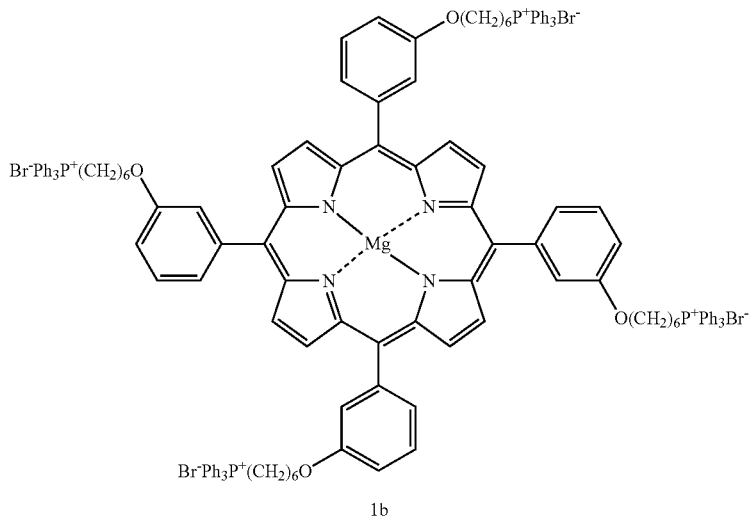

1b

Compound 6b (271 mg, 0.200 mmol) and triphenylphosphine (630 mg, 2.40 mmol) were dissolved in a mixed solvent of anhydrous chloroform (2 mL) and anhydrous acetonitrile (2 mL), and under dark conditions, the mixture was stirred at 70° C. for 48 hours under an argon atmosphere. The reaction solution was cooled to room temperature and concentrated. The crude product was washed with diethyl ether and filtrated. Recrystallization (methylene chloride/diethyl ether) gave magnesium-porphyrin complex 1b as a purple solid (yield: 337 mg, 70%).

$^1$H NMR (deuterated methanol, 600 MHz) 1.58-1.69 (m, 24H), 1.82 (br s, 8H), 3.35-3.38 (m, 8H), 4.15 (br s, 8H), 7.31 (d, J 8.4 Hz, 4H), 7.62-7.74 (m, 72H), 8.77-8.78 (m, 8H)

$^{13}$C NMR (deuterated methanol, 150 MHz) 22.4 (d, $J_{CP}$=49.9 Hz), 23.3, 26.3, 29.8, 31.0 (d, $J_{CP}$=15.9 Hz), 68.8, 114.0, 119.7 (d, $J_{CP}$=85.1 Hz), 122.6, 122.9, 128.3, 128.8, 131.4 (d, $J_{CP}$=12.3 Hz), 132.7, 134.6 (d, $J_{CP}$=9.2 Hz), 136.1, 146.3, 151.1, 158.5

$^{31}$P NMR (deuterated methanol, 243 MHz) 28.2

IR (potassiumbromide) 3055, 2939, 2862, 1593, 1516, 1477, 1435, 1331, 1285, 1254, 1180, 1111, 1061, 995, 934, 883, 795, 721, 691 cm$^{-1}$ 5,10,15,20-Tetrakis[3-(6-tributylammoniohexyloxy)phenyl]porphyrin magnesium(II) tetrabromide (1d) was synthesized. The reaction formula is shown below.

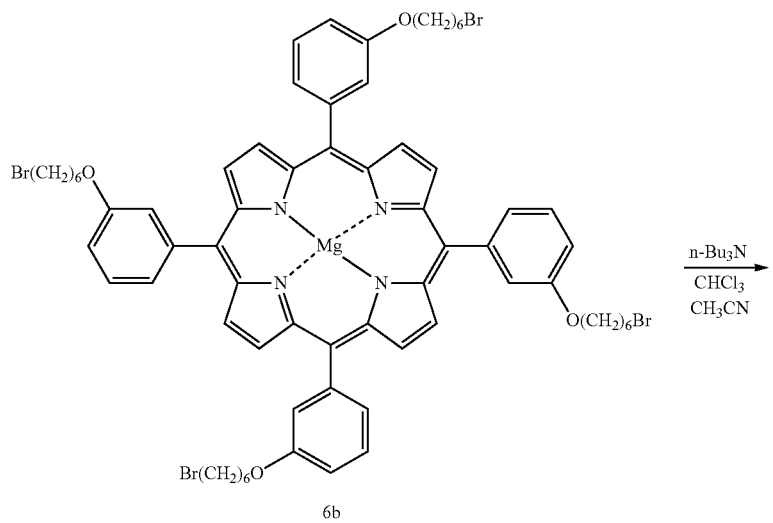

6b

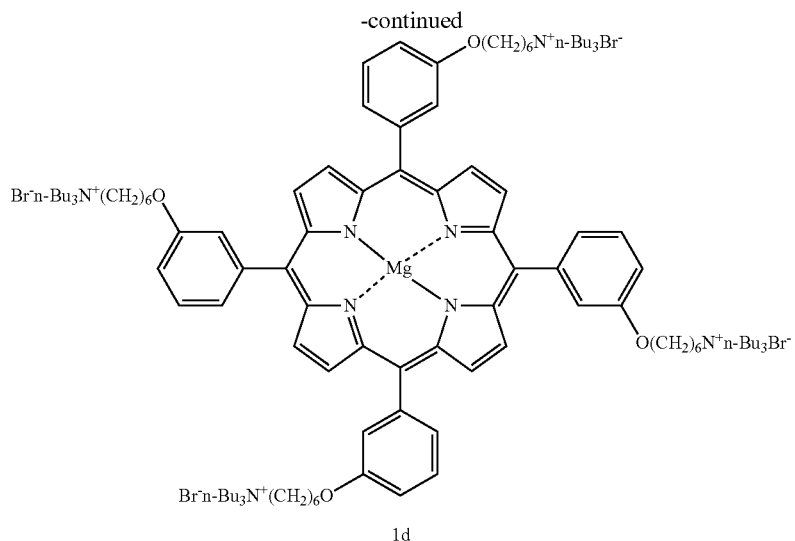

1d

Compound 6b (135 mg, 0.100 mmol) and tributylamine (0.57 mL, 2.4 mmol) were dissolved in a mixed solvent of anhydrous chloroform (1 mL) and anhydrous acetonitrile (1 mL), and under dark conditions, the mixture was stirred at 70° C. for 90 hours under an argon atmosphere. The reaction solution was cooled to room temperature and concentrated. The tributylamine layer was removed by a pipette. To the resulting mixture was added methylene chloride and the mixture was washed with water containing 0.5° hydrobromic acid and sodium bromide. The mixture was dried over sodium sulfate and concentrated. Recrystallization (methylene chloride/diethyl ether) gave magnesium-porphyrin complex 1d (purple solid) (yield: 157 mg, 75%).

$^1$H NMR (deuterated methanol, 600 MHz) 0.93-1.01 (m, 36H), 1.32-1.36 (in, 24H), 1.45-1.50 (m, 8ll), 1.57-1.71 (m, 40H), 1.89-1.95 (m, 8H), 3.14-3.24 (m, 32H), 4.21 (br s, 8H), 7.34 (dd, J=1.8, 8.6 Hz, 4H), 7.63 (t, J=7.9 Hz, 4H), 7.74-7.75 (m, 4H), 7.78 (d, J=6.5 Hz, 4H), 8.81-8.82 (m, 8H)

$^{13}$C NMR (deuterated methanol, 150 MHz) 14.0, 20.6, 22.6, 22.7, 24.7, 26.6, 26.9, 30.1, 59.3, 68.9, 114.2, 122.6, 122.8, 128.3, 128.8, 132.7, 146.4, 151.2, 158.6

IR (potassium bromide) 3038, 2963, 2876, 1597, 1578, 1474, 1431, 1383, 1333, 1279, 1184, 1165, 997, 937, 880, 799, 727, 710, 694 cm$^{-1}$ HRMS (ESI) calcd for $C_{116}H_{180}{}^{79}Br{}^{81}Br_2MgN_8O_4$ 2014.1487. Found 2014.1243 (M−Br)

5,10,15,20-Tetrakis[3-(8-bromooctyloxy)phenyl]porphyrin (5b) was synthesized. The reaction formula is shown below.

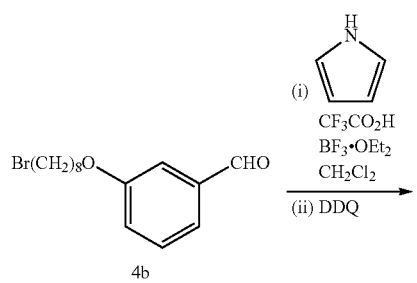

4b

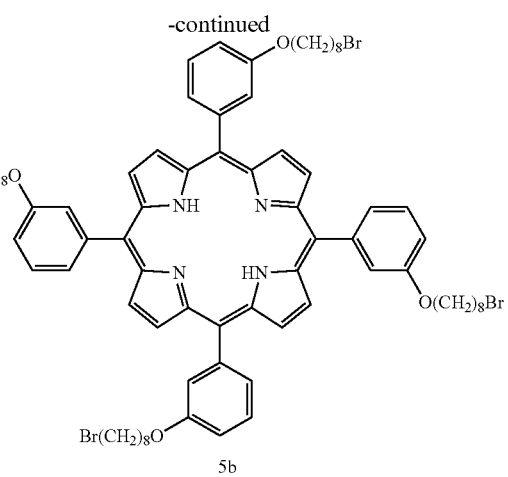

5b

A solution of pyrrole (0.81 mL, 12 mmol) and 3-(8-bromooctyloxy)benzaldehyde (4b) (3.66 g, 11.7 mmol) dissolved in anhydrous methylene chloride (1.2 L) was bubbled with argon, and to the mixture were added boron trifluoride-diethyl etherate complex (15 μL, 0.12 mmol) and trifluoroacetic acid (0.78 mL, 11 mmol). The mixed solution was stirred at room temperature for 4 hours under dark conditions. 2,3-Dichloro-5,6-dicyano-1,4-benzoquinone (2.66 g, 11.7 mmol) was added and the mixture was stirred at room temperature for 13 hours. To the reaction mixture was added triethylamine (1.2 mL, 8.6 mmol) and the mixture was concentrated. The concentrate was purified by silica gel column chromatography [chloroform/hexane (4:3)], to give compound 5b (highly viscous purple solid) (yield: 2.24 g, 53%).

$^1$H NMR (deuterochloroform, 600 MHz) −2.79 (s, 2H), 1.35-1.46 (m, 24H), 1.50-1.54 (m, 8H), 1.82-1.90 (m, 16H), 3.38 (t, J=6.8 Hz, 8H), 4.15 (t, J=6.5 Hz, 8H), 7.33 (dd, J=2.0, 8.4 Hz, 4H), 7.64 (t, J=7.9 Hz, 4H), 7.78 (s, 4H), 7.81 (d, J=7.3 Hz, 4H), 8.91 (s, 8H)

$^{13}$C NMR (deuterochloroform, 150 MHz, 50° C.) 26.0, 28.1, 28.6, 29.2, 29.4, 32.8, 33.6, 68.3, 114.3, 120.0, 121.4, 127.4, 127.6, 131.1, 143.5, 146.8, 157.6

IR (methylene chloride) 3317, 3031, 2932, 2862, 1597, 1466, 1435, 1396, 1350, 1281, 1180, 1042, 995, 980, 918, 872, 802, 748, 702, 640 cm$^{-1}$ MS (FAB) calcd for $C_{76}H_{91}{}^{79}Br_2{}^{81}Br_2N_4O_4$ 1443.4. Found 1443.4 (M+H)

5, 10, 15, 20-Tetrakis [3-(8-bromooctyloxy)phenyl]porphyrin magnesium (6c) was synthesized. The reaction formula is shown below.

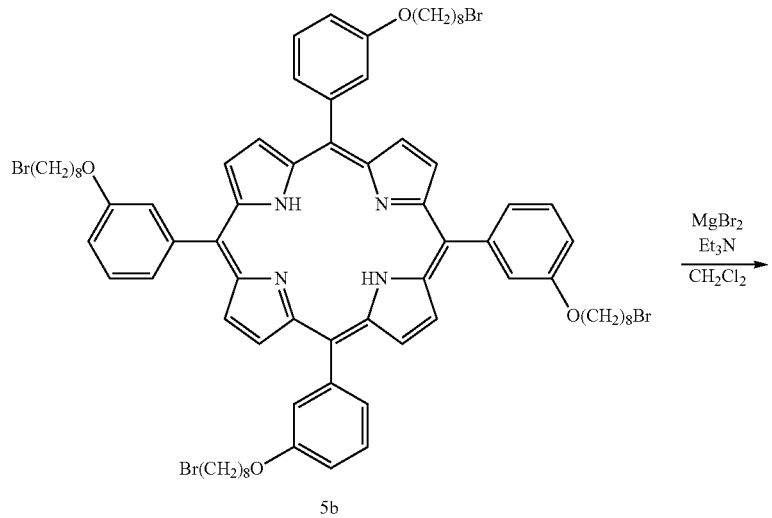

5b

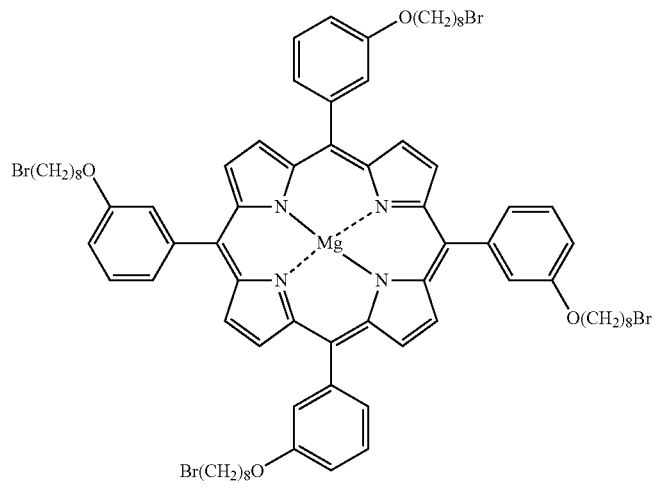

6c

Under a nitrogen atmosphere, a mixture of compound 5b (588 mg, 0.407 mmol) and magnesium bromide (752 mg, 4.09 mmol) in anhydrous methylene chloride (34 mL) was stirred at room temperature for 5 min. Triethylamine (3.4 mL, 24 mmol) was added and the mixture was stirred at room temperature for 30 min. The mixed solution was washed with 0.5% hydrochloric acid and water. The mixture was dried over sodium sulfate and concentrated. Recrystallization (methylene chloride/hexane) gave compound 6c (purple solid) (yield: 547 mg, 92%).

$^1$H NMR (deuterochloroform, 600 MHz) 1.33-1.52 (m, 32H), 1.80-1.85 (m, 16H), 3.36 (t, J=6.8 Hz, 8H), 4.03-4.09 (m, 8H), 7.24-7.25 (m, 4H), 7.59 (t, J=7.9 Hz, 4H), 7.73 (br s, 4H), 7.80 (d, J=7.2 Hz, 4H), 8.91 (s, 8H)

$^{13}$C NMR (deuterochloroform, 150 MHz) 25.7, 25.76, 25.80, 25.83, 28.0, 28.59, 28.60, 28.9, 28.96, 29.04, 29.07, 29.10, 32.7, 33.9, 68.3, 113.76, 113.84, 121.3, 121.4, 126.9, 127.8, 131.9, 144.8, 149.7, 156.5, 156.6 (atropisomer signals were observed)

IR (methylene chloride) 3047, 2936, 2858, 1597, 1576, 1518, 1472, 1431, 1391, 1333, 1285, 1265, 1207, 1184, 1165, 1067, 999, 937, 870, 800, 785, 756, 708, 644 cm$^{-1}$ Anal. Calcd for $C_{76}H_{88}{}^{79}Br_2MgN_4O_4$: C, 62.29; H, 6.05; N, 3.82. Found: C, 62.24; H, 5.97; N, 3.57

HRMS (FAB) calcd for $C_{16}H_{89}{}^{79}Br_2{}^{81}Br_2MgN_4O_4$ 1465.3. Found 1465.4 (M+H)

5,10,15,20-Tetrakis[3-(8-tributylammoniooctyloxy)phenyl]porphyrin magnesium (II) tetrabromide (1e) was synthesized. The reaction formula is shown below.

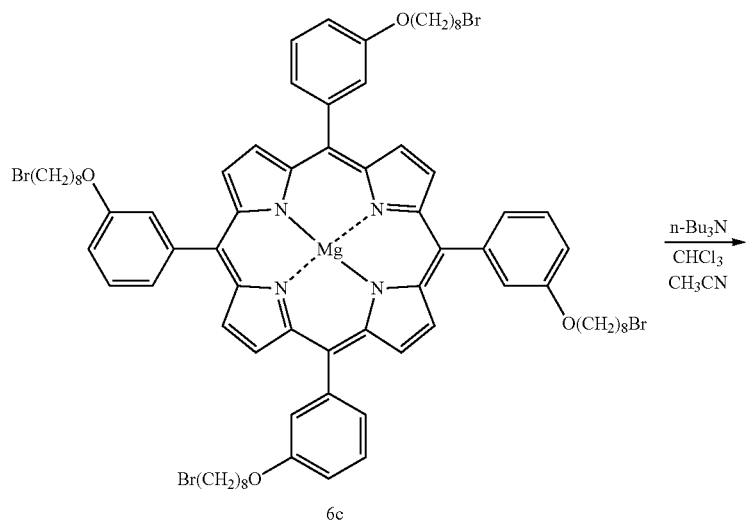

6c

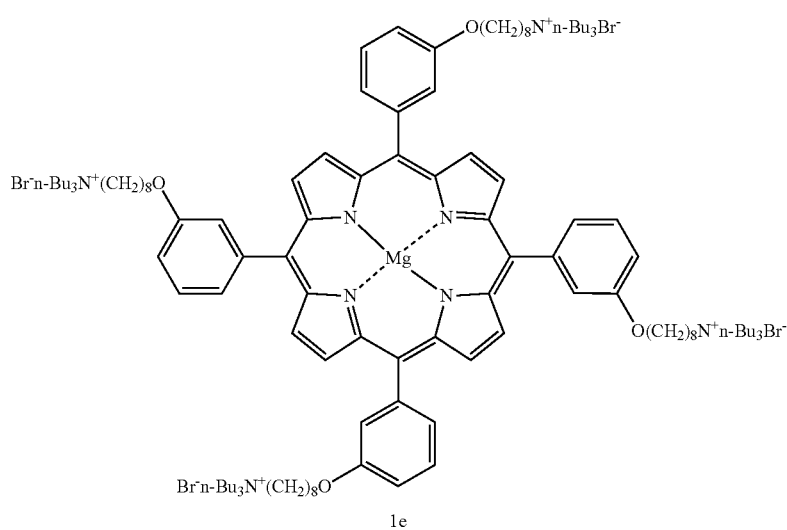

1e

Compound 6c (147 mg, 0.100 mmol) and tributylamine (0.57 mL, 2.4 mmol) were dissolved in a mixed solvent of anhydrous chloroform (1 mL) and anhydrous acetonitrile (1 mL), and under dark conditions, the mixture was stirred at 70° C. for 92 hours under an argon atmosphere. The reaction solution was cooled to room temperature and concentrated. The tributylamine layer was removed by a pipette. To the mixture was added methylene chloride, and the mixture was washed with water containing 0.5% hydrobromic acid and sodium bromide. The mixture was dried over sodium sulfate and concentrated. Recrystallization (methylene chloride/diethyl ether) gave magnesium-porphyrin complex 1e (purple solid) (yield: 187 mg, 85%).

$^1$H NMR (deuterated methanol, 600 MHz) 0.90-0.99 (m, 36H), 1.21-1.52 (m, 88H), 1.84-1.87 (m, 8H), 2.98-3.00 (m, 32H), 4.16 (br s, 8H), 7.31 (d, J=8.3 Hz, 4H), 7.62 (t, J=7.8 Hz, 4H), 7.73 (br s, 4H), 7.77 (br s, 4H), 8.85 (s, 8H)

$^{13}$C NMR (deuterated methanol, 150 MHz) 14.0, 20.5, 22.6, 24.6, 27.0, 27.1, 29.9, 30.1, 30.4, 59.2, 59.4, 69.2, 114.2, 122.6, 122.8, 128.3, 128.8, 132.8, 146.4, 151.2, 158.7

IR (potassium bromide) 3038, 2939, 2876, 1597, 1578, 1474, 1433, 1383, 1333, 1281, 1207, 1184, 1165, 997, 937, 880, 799, 712, 696 cm$^{-1}$ HRMS (ESI) calcd for $C_{124}H_{196}{}^{79}Br^{81}Br_2MgN_8O_4$ 2126.2739. Found 2126.2368 (M−Br)

Cyclic carbonates were synthesized using a zinc-porphyrin complex (1a or 1c) and a magnesium-porphyrin complex (1b, 1d or 1e) prepared as described above, as a catalyst.

Example 1

A cyclic carbonate was synthesized using zinc-porphyrin complex 1a as a catalyst. The reaction formula is shown below.

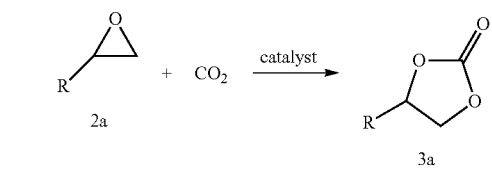

-continued

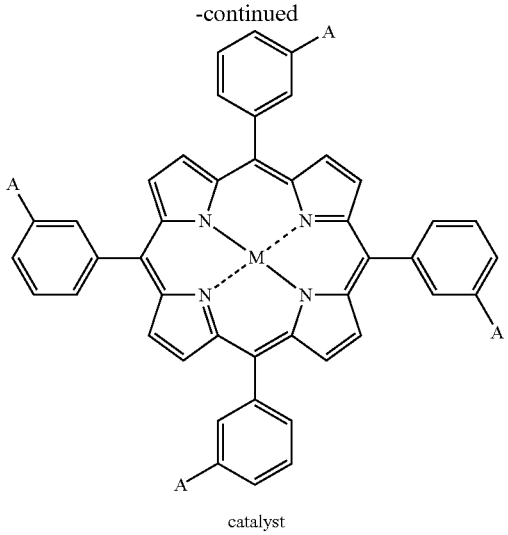

catalyst

1a: M = Zn, A = O(CH$_2$)$_6$P$^+$Ph$_3$Br$^-$
1b: M = Mg, A = O(CH$_2$)$_6$P$^+$Ph$_3$Br$^-$
1c: M = Zn, A = O(CH$_2$)$_6$N$^+$n-Bu$_3$Br$^-$
1d: M = Mg, A = O(CH$_2$)$_6$N$^+$n-Bu$_3$Br$^-$
1e: M = Mg, A = O(CH$_2$)$_8$N$^+$n-Bu$_3$Br$^-$ wherein R is a n-butyl group.

in a 30 mL autoclave were placed epoxide 2a (10.0 mmol) and zinc-porphyrin complex 1a as a catalyst [0.001 mmol (0.01 mol % to 2a)], and the autoclave was filled with carbon dioxide to a pressure of 1 MPa. The mixture was stirred at 120° C. for 3 hours. The autoclave was cooled in an ice bath for 30 min, and then excessive carbon dioxide was purged. To the crude product, 2-methoxynaphthalene was added as an internal standard, and then an NMR yield was determined. An yield of cyclic carbonate 3a was 80%. The reaction conditions and the yield are also shown in Table 1.

Examples 2 to 15

Cyclic carbonates 3a were synthesized and yields were determined as describe for Example 1, except that the type and the amount of a catalyst used, a pressure after carbon dioxide charge and a reaction time were as shown in Table 1. Table 1 shows NMR yields for these examples.

TABLE 1

| Entry | Catalyst[a] | Loading[b] (mol %) | CO$_2$ (MPa) | Time (h) | Yield (%) |
|---|---|---|---|---|---|
| Example 1 | 1a | 0.01 | 1.0 | 3 | 80 |
| Example 2 | 1b | 0.01 | 1.0 | 3 | 68 |
| Example 3 | 1c | 0.01 | 1.0 | 3 | 82 |
| Example 4 | 1d | 0.01 | 1.0 | 3 | 97 |
| Example 5 | 1a | 0.005 | 1.0 | 3 | 24 |
| Example 6 | 1b | 0.005 | 1.0 | 3 | 16 |
| Example 7 | 1c | 0.005 | 1.0 | 3 | 80 |
| Example 8 | 1d | 0.005 | 1.0 | 3 | 88 |
| Example 9 | 1d | 0.005 | 1.3 | 3 | 94 |
| Example 10 | 1d | 0.005 | 1.5 | 3 | 95 |
| Example 11 | 1d | 0.005 | 1.7 | 3 | 99 |
| Example 12 | 1d | 0.001 | 1.7 | 24 | 91 |
| Example 13 | 1d | 0.0008 | 1.7 | 24 | 83 |
| Example 14 | 1d | 0.003 | 1.5 | 9 | 98 |
| Example 15 | 1e | 0.002 | 1.0 | 21 | 82 |

[a] the structure of the catalyst used is shown in the reaction formula in Example 1.
[b] the amount of the catalyst.

Examples 16 to 20

Cyclic carbonates (3a, 3b, 3c, 3d, 3e) were synthesized as described in Example 1, except that a catalyst was magnesium-porphyrin complex 1d (0.005 mol % to an epoxide), a pressure after carbon dioxide charge was 1.5 MPa and the type of an epoxide and a reaction Lime were as shown in Table 2. Each compound obtained was purified by silica gel column chromatography and an isolation yield was determined. The results are shown in Table 2.

TABLE 2

| | Substrate | Product | Time (h) | Yield (%) |
|---|---|---|---|---|
| Example 16 | 2a (n-Bu epoxide) | 3a | 3 | 99 |
| Example 17 | 2b (Me epoxide) | 3b | 6 | 99 |
| Example 18 | 2c (n-Oct epoxide) | 3c | 6 | 93 |
| Example 19 | 2d (Ph epoxide) | 3d | 6 | 75 |
| Example 20 | 2e (Cl epoxide) | 3e | 6 | 95 |

Example 21

A cyclic carbonate was synthesized using magnesium-porphyrin complex TTP (Mg) as a catalyst and tetraphenylphosphonium bromide (TPPB) as a co-catalyst. The reaction formula is shown below.

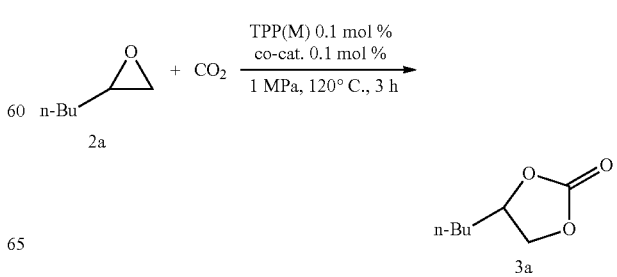

-continued

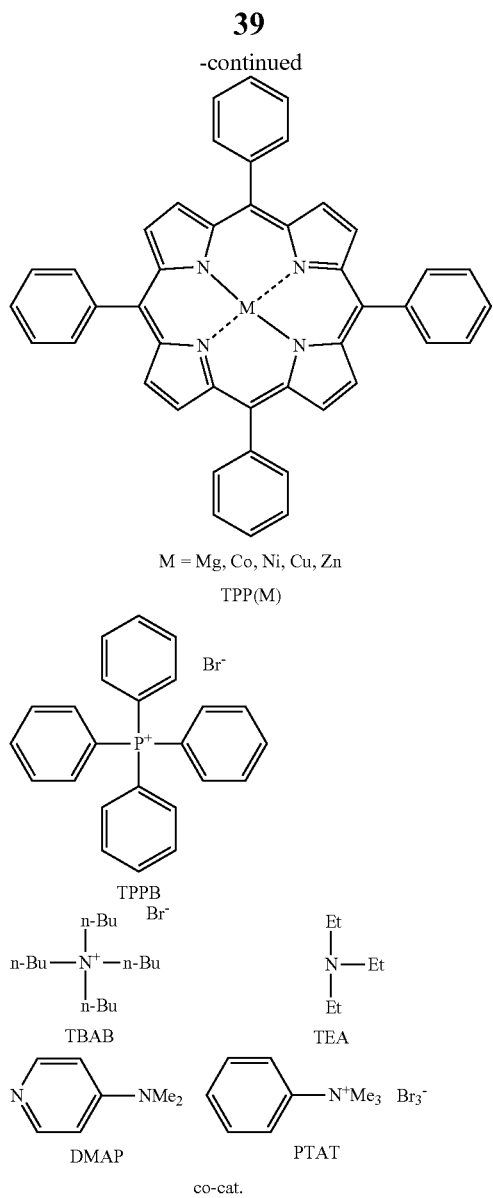

M = Mg, Co, Ni, Cu, Zn
TPP(M)

co-cat.

In a 30 mL autoclave were placed epoxide 2a (10.0 mmol) and magnesium-porphyrin complex TPP (Mg) as a catalyst [0.01 mmol (0.1 mol % to 2a)], and the autoclave was filled with carbon dioxide to a pressure of 1 MPa. The mixture was stirred at 120° C. for 3 hours. The autoclave was cooled in an ice bath for 30 min, and then excessive carbon dioxide was purged. To the crude product, 2-methoxynaphthalene was added as an internal standard, and then an NMR yield was determined. An yield of cyclic carbonate 3a was 94%. The yield is shown in Table 3 and also in FIG. 1.

Examples 22 to 26 and Comparative Examples 1 to 24

Cyclic carbonates 3a were synthesized and NMR yields were determined as described in Example 21, except that the types of a catalyst and a co-catalyst were as shown in Table 3. NMR yields for these examples are shown in Table 2 and FIG. 1.

TABLE 3

| Entry | TPP(M)[a] | Co-cat.[b] | Yield (%) |
|---|---|---|---|
| Example 21 | Mg | TPPB | 94 |
| Example 22 | Mg | TBAB | 93 |
| Example 23 | Mg | DMAP | 85 |
| Example 24 | Zn | TPPB | 93 |
| Example 25 | Zn | TBAB | 93 |
| Example 26 | Zn | DMAP | 54 |
| Comparative Example 1 | Mg | PTAT | 6 |
| Comparative Example 2 | Mg | TEA | 4.5 |
| Comparative Example 3 | Co | TPPB | 7 |
| Comparative Example 4 | Co | TBAB | 20 |
| Comparative Example 5 | Co | DMAP | 5 |
| Comparative Example 6 | Co | PTAT | 1 |
| Comparative Example 7 | Ni | TPPB | 33 |
| Comparative Example 8 | Ni | TBAB | 13 |
| Comparative Example 9 | Ni | DMAP | 6 |
| Comparative Example 10 | Ni | PTAT | 0.4 |
| Comparative Example 11 | Cu | TPPB | 34 |
| Comparative Example 12 | Cu | TBAB | 14 |
| Comparative Example 13 | Cu | DMAP | 5 |
| Comparative Example 14 | Cu | PTAT | 0.1 |
| Comparative Example 15 | Zn | PTAT | 1 |
| Comparative Example 16 | — | TPPB | 6 |
| Comparative Example 17 | — | TBAB | 13 |
| Comparative Example 18 | — | DMAP | 5 |
| Comparative Example 19 | — | PTAT | 0.3 |
| Comparative Example 20 | Mg | — | 0.4 |
| Comparative Example 21 | Co | — | 5 |
| Comparative Example 22 | Ni | — | 0 |
| Comparative Example 23 | Cu | — | 0.1 |
| Comparative Example 24 | Zn | — | 0.5 |

[a]the structure of each catalyst is shown in the reaction formula in Example 21.
[b]the structure of each co-catalyst is shown in the reaction formula in Example 21.

Example 27 to 29

Cyclic carbonates 3a were synthesized and NMR yields were determined as described in Example 21, except that a catalyst was as described below and its amount was as shown in Table 4, and a co-catalyst was TBAB and its amount was as shown in Table 4. The complexes were commercially available. The reaction conditions and NMR yields of these examples are shown in Table 4.

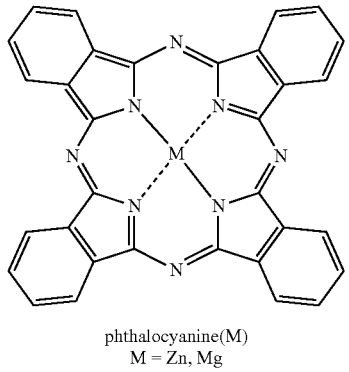

phthalocyanine(M)
M = Zn, Mg

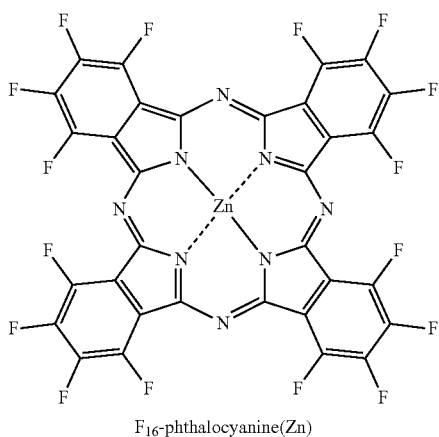

F$_{16}$-phthalocyanine(Zn)

TABLE 4

| Entry | Catalyst | Amount (mol %) | Co-catalyst | Amount (mol %) | Carbon dioxide (MPa) | Time (h) | NMR yield (%) |
|---|---|---|---|---|---|---|---|
| Example 27 | phthalocyanine(Zn) | 0.03 | TBAB | 0.03 | 1.0 | 3 | 19 |
| Example 28 | phthalocyanine(Mg) | 0.01 | TBAB | 0.01 | 1.0 | 3 | 35 |
| Example 29 | F$_{16}$-phthalocyanine(Zn) | 0.03 | TBAB | 0.03 | 1.0 | 3 | 17 |

The invention claimed is:

1. A metalloporphyrin complex represented by general formula (5):

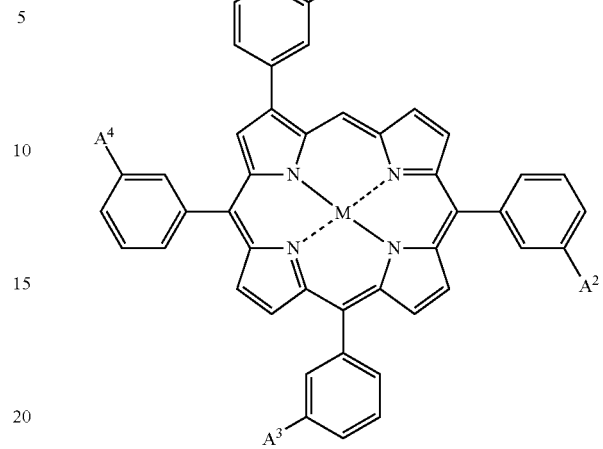

wherein M is metal; $A^1$ to $A^4$ are independently of each other a substituent represented by general formula (2):

$$-D-E^+X^- \qquad (2)$$

wherein D is a divalent organic group having 2 to 20 carbon atoms; $E^+$ is a quaternary ammonium group or quaternary phosphonium group having 3 to 60 carbon atoms; and X is a halogen atom.

2. The metalloporphyrin complex as claimed in claim 1, wherein in general formula (2), $E^+$ represents general formula (3):

wherein G is a nitrogen atom or phosphorus atom; and $R^1$ to $R^3$ are independently of each other a monovalent organic group having 1 to 20 carbon atoms; or $R^1$ to $R^3$ may be linked together to form a ring.

3. The metalloporphyrin complex as claimed in claim 1, wherein in general formula (2), D is an organic group represented by general formula (4):

$$-(CH_2)_a-J-(CH_2)_b- \qquad (4)$$

wherein J is an oxygen atom, —CO—O—, —O—CO—, a sulfur atom, —O—CO—NH—, —NH—CO—O—, —CO—NH—, —NH—CO— or a single bond; "a" is an integer of 0 or more; and "b" is an integer of 1 or more.

4. A process for manufacturing the metalloporphyrin complex as claimed in claim 1, comprising reacting a porphyrin represented by general formula (6'):

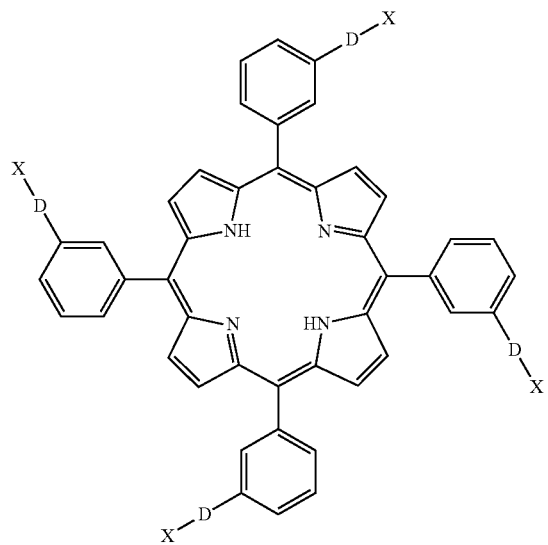

(6')

wherein D and X are as defined for general formula (2), with a salt of metal M, to form a metal complex represented by general formula (7'):

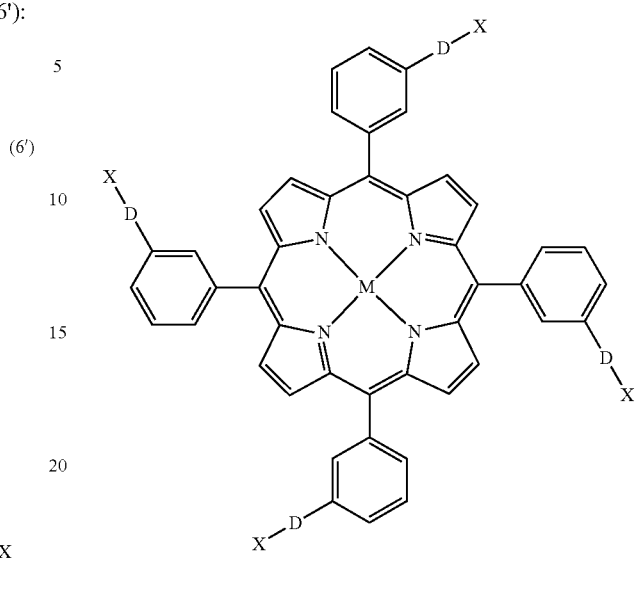

(7')

wherein M is as defined in general formula (1); and D and X are as defined in general formula (2); and then reacting the metal complex with a tertiary amine or tertiary phosphine to provide the metalloporphyrin complex represented by general formula (1).

5. A carbon dioxide fixation catalyst comprising the metalloporphyrin complex as claimed in claim 1.

* * * * *

UNITED STATES PATENT AND TRADEMARK OFFICE
CERTIFICATE OF CORRECTION

PATENT NO. : 9,211,534 B2
APPLICATION NO. : 14/345657
DATED : December 15, 2015
INVENTOR(S) : Tadashi Ema et al.

Page 1 of 1

It is certified that error appears in the above-identified patent and that said Letters Patent is hereby corrected as shown below:

Claims

Column 42, Claim 1, Lines 1-22: replace

"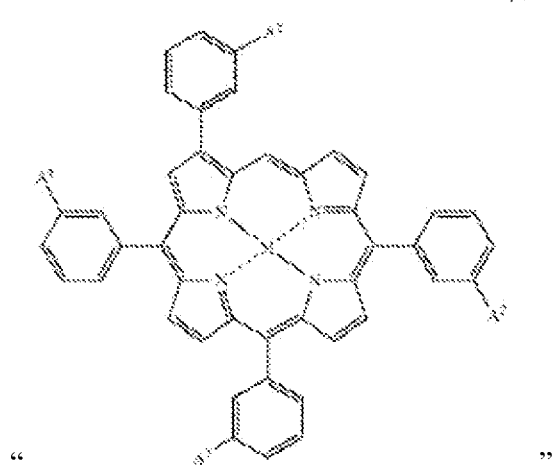"

with

"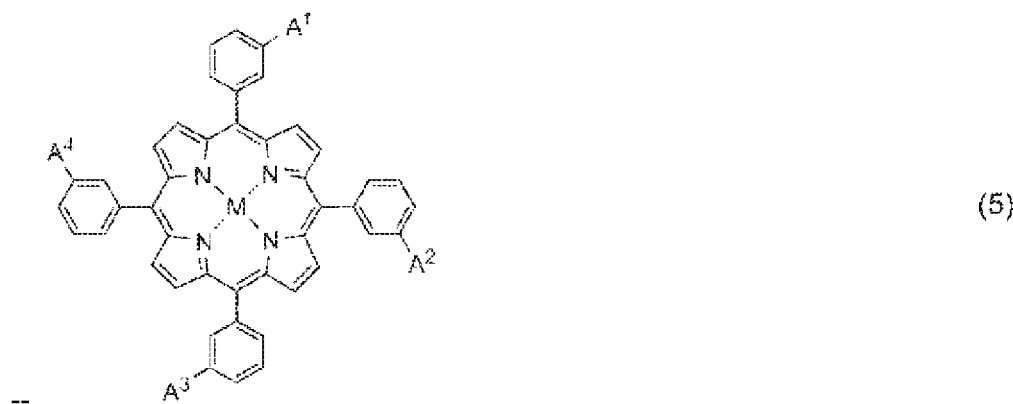" (5)

-- --

Signed and Sealed this
Tenth Day of May, 2016

Michelle K. Lee
*Director of the United States Patent and Trademark Office*